US009957325B2

(12) United States Patent
Li et al.

(10) Patent No.: US 9,957,325 B2
(45) Date of Patent: May 1, 2018

(54) SYNTHETIC ANTIBODY MIMIC PEPTIDES

(71) Applicant: Formurex, Inc., Stockton, CA (US)

(72) Inventors: Xiaoling Li, Dublin, CA (US); Jerry Tsai, stockton, CA (US); Bhaskara Rao Jasti, Stockton, CA (US); Hyun Joo, Stockton, CA (US); Yu Zheng, Stockton, CA (US); Dan Su, Fremont, CA (US); Sameer Sachdeva, Piscataway, NJ (US)

(73) Assignee: Formurex, Inc., Stockton, CA (US)

( * ) Notice: Subject to any disclaimer, the term of this patent is extended or adjusted under 35 U.S.C. 154(b) by 0 days. days.

(21) Appl. No.: 14/882,436

(22) Filed: Oct. 13, 2015

(65) Prior Publication Data

US 2017/0101474 A1 Apr. 13, 2017

(51) Int. Cl.
*A61K 38/00* (2006.01)
*G01N 33/74* (2006.01)
*C07K 16/28* (2006.01)

(52) U.S. Cl.
CPC ......... *C07K 16/2863* (2013.01); *G01N 33/74* (2013.01); *A61K 38/00* (2013.01); *C07K 2318/00* (2013.01); *G01N 2333/71* (2013.01)

(58) Field of Classification Search
CPC ..... C07K 16/2863; A61K 38/00; G01N 33/74
See application file for complete search history.

(56) References Cited

U.S. PATENT DOCUMENTS

2013/0330335 A1    12/2013  Bremel et al.

FOREIGN PATENT DOCUMENTS

| CA | 2867188 A1 | 9/2013 | |
|---|---|---|---|
| WO | WO 2014/202616 | * 12/2014 | ............ C07K 14/37 |
| WO | 2015-138435 A9 | 9/2015 | |

OTHER PUBLICATIONS

Lai et al., 2012, Genome Sequence of Nitratireductor pacificus Type Strain pht-3B, Journal of Bacteriology, 194(24): 6958.*
Lai et al., 2012, Journal of Bacteriology, 2 page alignment from SCORE.*
Paterson et al., 2012, Repeated polyploidization of Gossypium genomes and the evolution of spinnable cotton fibres, Nature, 492: 423-428.*
Paterson et al., 2012, Nature, 3 page alignment from SCORE.*
Wu, 2014, WO2014/202616, 6 page alignment from SCORE.*
Putnam, N. H. et al., The amphioxus genome and the evolution of the chordate karyotype; Nature; Jun. 19, 2008; vol. 453, pp. 1064-1072; Genbank supplement.
Sable, R. et al., Surfing the Protein-Protein Interaction Surface Using Docking Methods: Application to the Design of PPI Inhibitors; Molecules; Jun. 23, 2015; vol. 20, 11569-11603.
PCT/US16/56315, International Search Report and Written Opinion dated Apr. 4, 2017, 11 pages.

* cited by examiner

*Primary Examiner* — Amber D Steele
(74) *Attorney, Agent, or Firm* — Lin Sun-Hoffman

(57) ABSTRACT

The present disclosure relates to compositions and methods comprising peptide molecules that mimic the binding and functional properties of native antibodies relative to their respective targets. Some embodiments comprise peptide-drug conjugates (PDCs) comprising the mimic peptides disclosed herein. The targets of these mimic peptides include epidermal growth factor receptor (EGFR), and human epidermal growth factor receptor 2 (HER2), vascular endothelial growth factor (VEGF), programmed cell death protein 1 (PD-1), and programmed death-ligand 1 (PD-L1). The present disclosure comprises application of the knob-socket computational model to design antibody mimics for proteins.

7 Claims, 24 Drawing Sheets
(20 of 24 Drawing Sheet(s) Filed in Color)

FIG. 1A
FIG. 1B
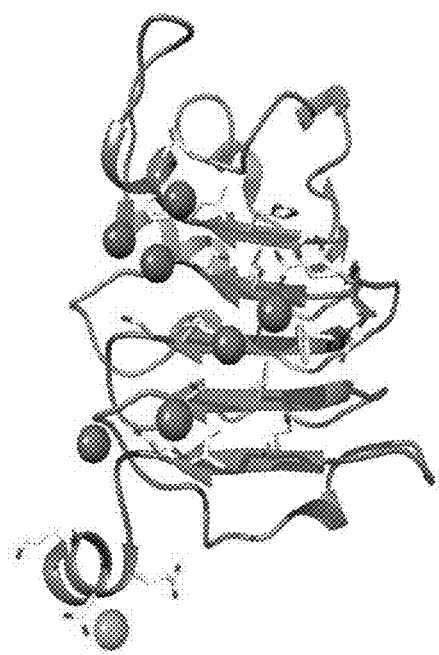
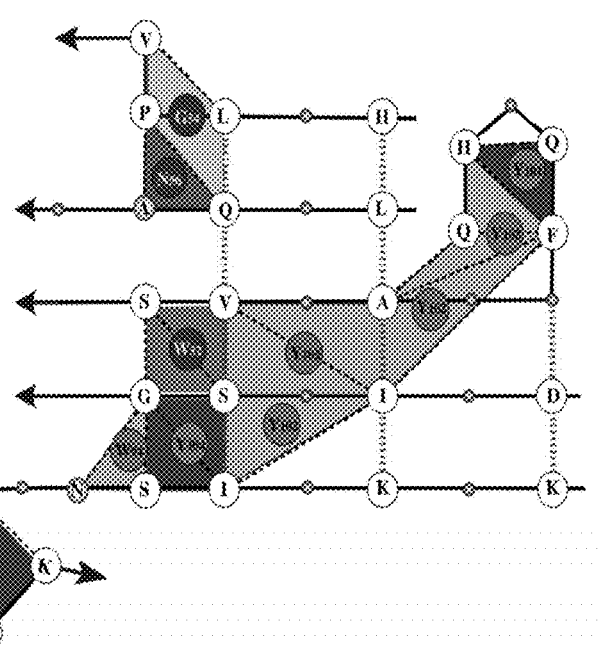
- CDR1
- CDR2
- CDR3

A                                      B

SYNTHETIC ANTIBODY MIMIC PEPTIDES

BACKGROUND

Field of the Disclosure

The present disclosure relates to compositions and methods comprising peptide molecules that mimic the binding and functional properties of native antibodies relative to their respective targets. These peptide molecules may be referred to herein synonymously as antibody mimics, mimic peptides, or simply mimics. Some embodiments comprise peptide-drug conjugates (PDCs) comprising the mimic peptides disclosed herein. Certain embodiments comprise methods of using the mimic peptides disclosed herein as targeting moieties and/or binding ligands, alone or as part of a PDC, such as in drug delivery or diagnostic assays. In various embodiments of the present disclosure, the targets of these mimic peptides can include but are not limited to epidermal growth factor receptor (EGFR), and human epidermal growth factor receptor 2 (HER2), vascular endothelial growth factor (VEGF), programmed cell death protein 1 (PD-1), and programmed death-ligand 1 (PD-L1).

SEQUENCE LISTING

This application hereby incorporates by reference the material of the electronic Sequence Listing filed concurrently herewith. The material in the electronic Sequence Listing is submitted as a text (.txt) file entitled "LXL002_ST25.txt" created on Oct. 13, 2015, which has a file size of 20 KB, and is herein incorporated by reference in its entirety.

Brief Description of Related Art

Antibodies, as well as their smaller constituent fragments, have found wide application for use in diagnostics and therapeutics. One example is the use of antibodies alone in treatment of diseases such as cancer. Another example is the use of an antibody as a composite part of an antibody-drug conjugate (ADC), wherein the antibody can act as the targeting agent in targeted drug delivery compositions and methods. Antibodies/antibody fragments are especially amenable for use as targeting agents because they are highly specific for their target receptors and bind with high affinity. A particular type of targeted drug delivery therapy is anti-cancer therapy. The primary goal of anti-cancer therapy generally is of course to kill cancer cells without affecting normal, healthy cells. Targeted drug delivery methods are particularly effective in treating cancer because they specifically target cancer cells which overexpress certain antigen receptors, without harming or with less harm to normal cells which do not express the antigens or do so to a lesser extent. In these targeted drug delivery methods generally an anti-cancer drug is attached to a targeting moiety, such as an antibody or antibody fragment, thus creating an ADC which targets and binds to the cell receptor and thus introduces the drug to the cell.

A number of monoclonal antibodies are currently known and approved for treating various diseases, such as cancer. These include cetuximab (trade name ERBITUX®, Bristol-Myers Squibb/Merck KGaA/Eli Lilly), which targets EGFR; pertuzumab (also known as 2C4, trade name PERJETA®, Genentech), which targets HER2; and, trastuzumab (trade names HERCLON® and HERCEPTIN®, Genentech), which also targets HER2. In the example of cancer treatment, the antibody selectively binds a target antigen on the cancer cell with high affinity, and exerts its effects by various means including blocking cell signaling, antibody-dependent cytotoxicity, or complement dependent cytotoxicity.

Antibody treatment alone, however, has proven inadequate in many cases, due to reasons including insufficient cell killing, resistance to the antibodies, etc. For this reason antibody treatment is frequently in conjunction with chemotherapy. One method of treatment is to administer separately an antibody and a drug. Another is the use of an antibody-drug conjugate (ADC), in which an antibody is linked (conjugated) to a drug compound. This brings together in one molecule the specificity and affinity of the antibody for a particular cell type, and the toxicity for that cell of a potent anti-cancer drug. In the case of cancer treatment, generally the antibody of the ADC targets a cell receptor that is overexpressed in tumor cells relative to normal, healthy cells. Thus, tumor cells are preferentially targeted for the cytotoxic effects of the drug.

At least two ADCs are currently in the market as therapeutic agents: brentuximab-vedotin (trade name ADCETRIS®, Seattle Genetics), in which brentuximab which targets CD30-expressing cells is conjugated to monomethyl auristatin E (MMAE), a potent anti-microtubule agent; and, ado-trastuzumab-emtansine (trade name KADCYLA®, Genentech), in which trastuzumab is conjugated to one or more DM1 molecules (DM1 being a derivative of maytansine comprising a linker moiety, as described below), an inhibitor of microtubule formation. Treatment of trastuzumab-resistant patients with the ADC trastuzumab-emtansine, for example, results in increased survival. See S. Verma et al., *N. Engl. J. Med.* (2012) 367:1783-1791.

ADCs generally comprise antibody, drug, and linker moieties, and may additionally comprise spacer, attachment, and other moieties. The choice of the drug and the linker that conjugates the antibody to the drug are key determinants of the activity and tolerability of the ADC. The linker should be such that it remains stable in the blood and before the ADC attaches to the target cell. Then, depending on the particular mode of action of the drug, it may be preferable that the linker remain intact upon antibody-receptor binding, or that it be cleaved at some point after binding; e.g., immediately after binding and before internalization of the ADC within the cell, or after internalization to release the drug inside the cell. Thioether linkers, for example, are relatively non-cleavable linkers—the mode of action of ADCs comprising these linkers depends on the degradation of the antibodies (not cleavage of the linker) to release the drug, which remains attached to the linker. As an example, the ADC ado-trastuzumab-emtansine uses a non-cleavable thioether linker to conjugate the maytansinoid drug to the antibody. As another example, linkers comprising hydrazone are destabilized at low pH and are thus cleaved in the low-pH environment of the cell lysosome, releasing drug from antibody. Gemtuzumab-ozogamicin (trade name MYLOTARG®, Wyeth), an ADC comprising a monoclonal antibody to CD33 in combination with the potent drug N-acetyl-γ-calicheamicin, is conjugated via a hydrazone linker which is selectively cleaved in the acidic intracellular environment of the cancer cell. As another example, linkers comprising disulphide bond(s) are destabilized in a reducing environment and are thus cleaved in the reducing environment of the cytosol, releasing drug from antibody.

Linkers that are cleaved by peptidases can also be used in ADCs, such as for example dipeptide linkers. As an example, a citrulline-valine linker is used in the ADC brentuximab-vedotin. Cleavage of this linker is achieved only by proteases inside the cancer cell lysosome, thus imparting a greater stability to this ADC outside the cell.

Generally, the cytotoxic agents currently used as the "drugs" in ADCs are highly potent, toxic and non-specific molecules which thus cannot be used in therapy alone because of their toxicity to normal, healthy cells. These cytotoxic agents include but are not limited to auristatins, maytansinoids and calcheamicins, with $IC_{50}$ values in the picomolar range. Monomethyl auristatin E (MMAE) is an auristatin which is a component of brentuximab-vedotin, as well as a number of ADCs in clinical trials. Mertansine, a maytansinoid, is a component of the approved ADC ado-trastuzumab-emtansine. Auristatins and maytansinoids exert their cytotoxic affect by binding to tubulin and inhibiting its polymerization, which leads to apoptosis of the target cell.

The mode of activity of ADCs generally is as follows. Upon binding of the antibody moiety to the target antigen (usually a cell receptor), the antigen and ADC undergo receptor-mediated endocytosis. After internalization within the cell, the ADC is degraded (which could occur in the lysosome or the cytosol, depending on the ADC), and the drug is released and causes the cytotoxic effect and hence cell death. The rate and extent of internalization are important factors, as they impact the efficacy of the ADC. Furthermore, the number of receptors on the cell is an important factor in ADC efficacy—clearly, ADCs specific for receptors that are overexpressed on certain cells, such as cancer cells, will result in preferential targeting of these cells.

The extensive use of full-length antibodies for applications such as treatment and targeted drug delivery, however, has been limited by various factors, including the high cost and time involved in producing antibodies, and their large molecular weight which presents several drawbacks, including their limited ability to penetrate tumor tissues, which is often a requirement in ADC systems for the effective toxicity of drugs that act intracellularly. Thus there is a need for alternatives to antibodies/antibody fragments, which should have binding specificity and affinity properties similar to the native antibody but not require the lengthy and complicated processes involved in generating antibodies, especially when they are to be used in therapy and/or as targeting agents.

Some synthetic alternatives to antibodies/antibody fragments have been developed. Although these have low molecular weight compared to antibodies, they are based on conventional, full-sized antibodies, and/or identified and derived through a long and tedious in vitro screening process. Therefore, not only are alternatives to antibodies/antibody fragments needed, but also methods of rationally designing (such as in silico) molecules that functionally mimic antibodies in their binding affinity for target.

The present disclosure describes compositions and methods comprising effective antibody mimic peptides, which overcome the limitations outlined above. The use of the antibody mimic peptides described herein include diagnostic agents, reagents, and targeting moieties in peptide-drug conjugates (PDCs), which are the equivalent of ADCs except that peptide mimics are used in place of antibodies, and are as effective as their corresponding ADCs.

SUMMARY

The present disclosure comprise an isolated peptide comprising at least one of a motif sequence $WX_1EX_2PX_3FYX_4YX_5A$ or the reverse of said motif sequence, said motif sequence having $N_N$ amino acids, wherein P is proline, W is tryptophan, E is glutamic acid, F is phenylalanine, Y is tyrosine, A is alanine, and each of $X_1$, $X_2$, $X_3$, $X_4$ and $X_5$ is any of 0 to 8 amino acids; and, wherein P is at amino acid position $N_N/2$ of the motif sequence (i.e., in the middle) or next thereto.

Other embodiments comprise the peptide $WX_1EX_2PX_3FYX_4YX_5A$, but wherein the FY in the motif sequence is replaced with YW, YL, YI, YV, YF, WY, LY, IY, VY, YY, TYY, TYW, TYL, TYI, TYV, TYF, TWY, TLY, TIY, TVY, or TFY, wherein T is threonine, L is leucine, I is isoleucine, and V is valine. In some embodiments the length of the motif sequence ranges from 7 to 25 amino acids. In some embodiments, the motif sequence comprises 7, 10, 15, 20, or 25 amino acids.

Some embodiments of the present disclosure comprise an isolated peptide comprising at least one motif sequence comprising a first sequence $QX_1SNX_2PARX_3TDX_4$, a second sequence $QX_5SNX_6PARX_7TDX_8GP$, the reverse of said first sequence, or the reverse of said second sequence, wherein the motif sequence has $N_N$ amino acids, wherein P is p line, Q is glutamine, S is serine, N is asparagine, A is alanine, R is arginine, T is threonine, D is aspartic acid, G is glycine, and each of $X_1$, $X_2$, $X_3$, $X_4$, $X_5$, $X_6$, $X_7$, and $X_8$ is any of 0 to 8 amino acids; and, wherein P is at amino acid position $N_N/2$ of the motif sequence in the middle) or next thereto. In some embodiments the length of this motif sequence ranges from 8 to 25 amino acids. In some embodiments, the motif sequence comprises 8, 10, 15, 20, or 25 amino acids.

Some embodiments comprise an isolated peptide comprising a sequence selected from group consisting of the sequences listed in Table 1; i.e., SEQ ID NO. 1, SEQ ID NO. 2, SEQ ID NO. 3, SEQ ID NO. 4, SEQ ID NO. 5, SEQ ID NO. 6 SEQ ID NO. 7, SEQ ID NO. 8, SEQ ID NO. 9, SEQ ID NO. 10, SEQ ID NO. 11, SEQ ID NO. 12, SEQ ID NO. 13, SEQ II) NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, and SEQ ID NO. 24.

Some embodiments comprise an isolated peptide comprising a sequence selected from group consisting of the sequences listed in Table SEQ II) NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45 and SEQ ID NO. 46.

Some embodiments comprise an isolated peptide comprising a sequence selected from group consisting of the sequences listed in Tables 8, 9 and 10; i.e., SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56, SEQ ID NO. 57, SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73. SEQ II) NO. 74, SEQ II) NO. 75. SEQ II) NO. 76 and SEQ ID NO. 77.

Some embodiments comprise one or more of the peptides described herein comprising a, motif that effectively targets EGFR or HER2. Some embodiments comprise a peptide as described above conjugated to a substance wherein the substance s a therapeutical or a detection moiety. In some embodiments the drug is an anti-cancer drug. In some embodiments the peptide is conjugated to MMAE. Some embodiments comprise a method for detecting a disease associated with EGFR, HER2, VEGF, PD-1, or PD-L1 expression, or a combination thereof, comprising the use of one or more of the peptides described herein.

Some embodiments of the present disclosure comprise a kit for research reagent or diagnosing a disease associated with EGFR, HER2, VEGF, PD-1, or PD-L1 expression, using of the peptides described herein. Some embodiments comprise a method for treating a disease associated with EGFR, HER2, VEGF, PD-1, or PD-L1 comprising the use of one or more of the peptides described herein and/or their conjugates. Some embodiments comprise methods of cell killing comprising a peptide conjugate as described herein.

Further embodiments of the present disclosure comprise methods of using peptides disclosed herein as delivery vehicles. In some embodiments, the methods comprise the use of peptides disclosed herein in protein-protein interactions. Specific embodiments comprise methods of targeted drug delivery, diagnostics, and/or therapeutics comprising the peptides disclosed herein. Some embodiments comprise methods of treating or preventing cancer comprising the peptides disclosed herein. Certain embodiments comprise peptide-drug conjugates (PDC) comprising one or more of the peptides disclosed herein conjugated to drug. Additional embodiments comprise targeted delivery agents comprising said peptide-drug conjugates. Some embodiments comprise therapeutic methods comprising said targeted delivery agents.

In another aspect, the present invention describes the application of the knob-socket computational model to design antibody mimics for proteins including EGFR, HER2, VGEF, PD-1, podoplanin, etc. The present invention provide a method for designing an antibody mimic peptide comprising identifying and mapping of binding surface based on interactions between antibody and epitope, and selecting the amino acids with high interaction frequency to form a peptide wherein the peptide is 10-30 amino acids in length. The antibody and epitope interaction is based on crystal structure information.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows a ribbon diagram of the cetuximab-EGFR epitope interface, and FIG. 1B shows a schematic diagram of the cetuximab-EGFR epitope interaction, mapping the various knobs and sockets.

DETAILED DESCRIPTION

Figure 2:
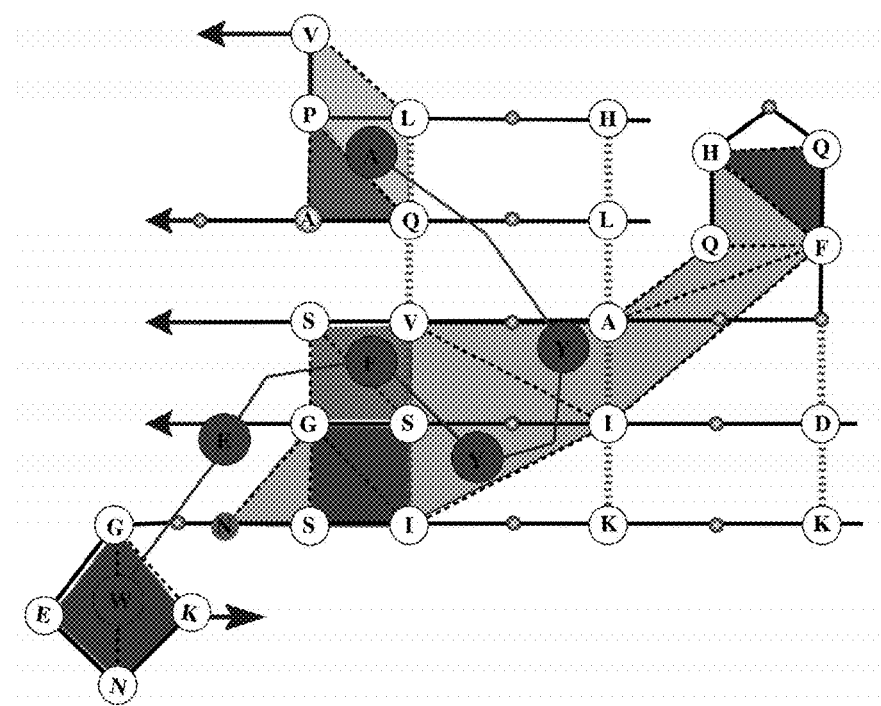
FIG. 2 shows a schematic diagram of an antibody mimic (WX$_1$EX$_2$FYX$_3$YX$_4$A, SEQ ID NO: 82)-EGFR epitope interaction, showing various knobs and sockets.

The present disclosure describes peptides that can serve as synthetic alternatives to antibodies and antibody fragments; i.e., antibody mimic peptides, or peptides. These peptides can be used in a wide variety of applications including, for example but without limitation, as targeting or delivery agents, in imaging, therapeutics and diagnostics, for various diseases or disorders, and as reagents in research. These peptides can be used alone or in conjunction with other compounds. As one example, they can be conjugated to drugs in targeted drug delivery systems, such as in peptide-drug conjugates (PDC) for treating cancer or other diseases. As yet another example, they can be conjugated to probes for diagnostic or research applications.

The present invention provides a rational and novel design of peptide antibody mimics based on the crystal structure and utilizing Knob-Socket computational design.

This model represents the complexities of packing between two molecules. There are three types of sockets: (1) free socket, favoring only intra-molecule packing; (2) filled socket, favoring interaction with knobs; and (3) non-socket, disfavoring secondary structure. The amino acid propensities in these three socket classes essentially represent an amino acid for structure in packing. The Knob-Socket model was applied to map and identify socket residues, and peptide sequences were designed based on the best fitting knobs into the sockets identified on the receptor epitopes.

Specifically, the invention dealt with the identification of the binding surface based on the interactions between antibody and epitope using crystal information from protein database or mapping the binding surface by simulation/modeling. After the identification and mapping of the binding surface, the surface is reduced to a two dimensional map by using the knob and socket model. Based on the probability of interactions between knobs and sockets, the antibody mimic molecules are designed by selecting the amino acids with high interaction frequency to form a peptide that is composed of 10 to 30 amino acids. After screening using the docking software Molecular Operating Environment (MOE), the antibody mimic molecules are then synthesized using a solid phase peptide synthesis approach. These molecules are characterized for their binding specificity, affinity, and potential biological functions.

Functional alternatives to full-length antibodies are known and include antibody fragments, synthetic peptides, and synthetic combinations of the two; e.g., Fab, F(ab')2, scFv, minibodies, peptibodies and antibody mimic peptides. However, the methods of identifying and designing these alternatives are still based on conventional antibodies and/or through long, tedious and costly screening techniques such as phage, ribosome and mRNA display.

The synthetic peptides disclosed herein have the functionality of known antibodies, and thus can be used in applications where currently an antibody would be used, with equivalent or better efficacy, while circumventing the above-described limitations. Two examples of such applications where a peptide of the present disclosure can be utilized are where an antibody itself is administered.

The invention also provides pharmaceutical compositions comprising a peptide of the invention and a pharmaceutically acceptable carrier. The pharmaceutical compositions comprising peptide of the invention are for use in, but not limited to, diagnosing, detecting, or monitoring a disorder; in preventing, treating, managing, or ameliorating a disorder or one or more symptoms thereof; and/or in research. In a specific embodiment, a composition comprises one or more peptides of the invention.

In another embodiment, the pharmaceutical composition comprises one or more peptides of the invention for treating a disorder in peptide activity is detrimental. Preferably, the prophylactic or therapeutic agents known to be useful for or having been or currently being used in the prevention, treatment, management, or amelioration of a disorder, such as cancer or a tumor, or one or more symptoms thereof. In accordance with these embodiments, the composition may further comprise of a carrier, diluent, or excipient.

The peptide of the invention can be incorporated into pharmaceutical compositions suitable for administration to a subject. Typically, the pharmaceutical composition comprises a peptide of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more peptide of the invention or the combination of one or more peptides of the invention and a prophylactic agent or therapeutic agent useful for preventing, managing, treating, or ameliorating a disorder or one or more symptoms thereof; e.g., reducing tumor angiogenesis, encapsulation in liposomes, microparticles, microcapsules, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed; e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and, 4,880,078; and PCT Publication Nos. WO 92/19244, WO 97/32572, WO 97/44013, WO 98/31346, and WO 99/66903, each of which is incorporated herein by reference in their entireties.

In one embodiment, a peptide of the invention, combination therapy, or a composition of the invention is administered using pulmonary drug delivery technology (see, e.g., Alkermes, Inc., Cambridge, Mass., US). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment. This may be achieved by, for example and not by way of limitation, local infusion, by injection, or by means of an implant, said implant being of a porous or non-porous material, including membranes and matrices, such as sialastic membranes, polymers, fibrous matrices, or collagen matrices. In one embodiment, an effective amount of one or more peptides of the invention antagonists is administered locally to the affected area to a subject to prevent, treat, manage, and/or ameliorate a disorder or a symptom thereof. In another embodiment, an effective amount of one or more peptides of the invention is administered locally to the affected area in combination with an effective amount of one or more therapies (e.g., one or more prophylactic or therapeutic agents) other than a peptide of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release. See, e.g., Langer, *Science,* 249: 1527-1533 (1990); Sefton, *CRC Crit. Rev. Biomed. Eng.,* 14: 201-240 (1987); Buchwald et al., *Surgery,* 88: 507-516 (1980); and, Saudek et al., *N. Engl. J. Med.,* 321: 574-579 (1989). In another embodiment, polymeric materials can be used to achieve controlled or sustained release of the therapies of the invention. See, e.g., Goodson, J. M, *Medical Applications of Controlled Release, Vol. II, Applications and Evaluations* (Langer and Wise, eds., CRC Press Inc., Boca Raton, 1984), chapter 6, pages 115-138; *Controlled Drug Bioavailability, Drug Product Design and Performance* (Smolen and Ball, eds., Wiley, New York, 1984); and, Langer and Peppas, *J. Macromol. Sci. Rev. Macromol. Chem. Phys.,* C23:61-126 (1983). See also, Levy et al., *Science,* 228:190-192 (1985); During et al., *Ann. Neurol.,* 25:351-356 (1989); Howard et al., *J. Neurosurg.,* 71:105-112 (1989); U.S. Pat. Nos. 5,679,377; 5,916,597; 5,912,015; 5,989,463; and, 5,128,326; and, PCT Publication Nos. WO 99/15154 and WO 99/20253. Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose. See, e.g., Goodson, *Medical Applications of Controlled Release* (1984), pages 115-138.

Controlled release systems are discussed in the review by Langer (*Science,* 249:1527-1533 (1990)). Any technique known to one of skill in the art can be used to produce sustained release formulations comprising one or more therapeutic agents of the invention. See, e.g., U.S. Pat. No. 4,526,938; PCT Publication Nos. WO 91/05548 and WO 96/20698; Ning et al., "Intratumoral Radioimmunotherapy of a Human Colon Cancer Xenograft Using a Sustained-Release Gel," *Radiother. Oncol.,* 39:179-189 (1996); Song et al., "Antibody Mediated Lung Targeting of Long-Circulating Emulsions," *PDA J. Pharm. Sci.Tech.,* 50:372-377 (1996); Cleek et al., "Biodegradable Polymeric Carriers for a bFGF Antibody for Cardiovascular Application," *Proceed. Intl. Symp. Control. Rel. Bioact. Mater.,* 24:853-854 (1997); and, Lam et al., "Microencapsulation of Recombinant Humanized Monoclonal Antibody for Local Delivery," *Proceed. Intl. Symp. Control Rel. Bioact. Mater.,* 24:759-760 (1997), each of which is incorporated herein by reference in their entireties.

A pharmaceutical composition of the invention is formulated to be compatible with its intended route of administration. Examples of routes of administration include, but are not limited to, parenteral (e.g., intravenous), intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences and Introduction to Pharmaceutical Dosage Forms,* 19*th ed.* (Mack Publishing Co., Easton, Pa., 1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant) or in a squeeze bottle. Moisturizers or humectants can also be added to pharmaceutical compositions and dosage forms if desired. Examples of such additional ingredients are well known in the art.

If a method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If a method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or, wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and, preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

A method of the invention may comprise pulmonary administration; e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and, 4,880,078; and, PCT Publication Nos. WO 92/19244, WO 97/32572, WO 97/44013, WO 98/31346, and WO 99/66903, each of which is incorporated herein by reference in their entireties. In a specific embodiment, an antibody of the invention, combination therapy, and/or composition of the invention is administered using Alkermes pulmonary drug delivery technology (Alkermes, Inc., Cambridge, Mass., US).

A method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

A method of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

Methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, a composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml, or at least 100 mg/ml. The liquid form should be stored at between 2° C. and 8° C. in its original container.

The peptide of the invention can be incorporated into a pharmaceutical composition suitable for parenteral administration. Preferably, the peptide will be prepared as an injectable solution containing 0.1-250 mg/ml. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In an embodiment, a peptide described herein is administered by intravenous infusion or injection. In another embodiment, the peptide is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The peptide of the present invention can be administered by a variety of methods known in the art, although for many therapeutic applications, the preferred route/mode of administration is subcutaneous injection, intravenous injection, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed. (Marcel Dekker, Inc., New York, 1978).

In certain embodiments, a binding protein of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a binding protein of the invention is coformulated with and/or coadministered with one or more additional therapeutic agents that are useful for treating disorders in which peptide activity is detrimental. Furthermore, one or more binding proteins of the invention may be used in combination with two or more of the foregoing therapeutic agents. Such combination therapies may advantageously utilize lower dosages of the administered therapeutic agents, thus avoiding possible toxicities or complications associated with the various monotherapies.

In another aspect, this invention provides a method of treating (e.g. curing, suppressing, ameliorating, delaying, or preventing the onset of, or preventing recurrence or relapse of) or preventing a tumor in a subject. The method includes administering to a subject a peptide, in an amount sufficient to treat or prevent the tumor or cancer.

It should be understood that peptides claimed in the invention can also be used alone or in combination with an additional agent; e.g., a therapeutic agent, said additional agent being selected by the skilled practitioner for its intended purpose. For example, the additional agent can be a therapeutic agent that is recognized in the art as being useful to treat a cancer, tumor, or other disease. The additional agent also can be an agent that imparts a beneficial attribute to the therapeutic composition; e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents, if the combination is such that the formed composition can perform its intended function.

Preferred combinations of therapeutic agents may interfere at different points in the pro-tumorigenic or pro-angiogenic signaling pathways. Preferred examples of therapeutic agents useful in the methods and compositions of the invention include antineoplastic agents, radiotherapy, and chemotherapy such as DNA alkylating agents, cisplatin, carboplatin, anti-tubulin agents, paclitaxel, docetaxel, taxol, doxorubicin, gemcitabine, gemzar, anthracyclines, adriamycin, topoisomerase I inhibitors, topoisomerase II inhibitors, 5-fluorouracil (5-FU), leucovorin, irinotecan, receptor tyrosine kinase inhibitors (e.g., erlotinib, gefitinib), COX-2 inhibitors (e.g., celecoxib), and kinase inhibitors.

The peptide(s) of the invention may also be administered in combination with agents, such as methotrexate, 6-MP, azathioprine sulphasalazine, mesalazine, olsalazine chloroquinine/hydroxychloroquine, penicillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™) and p55TNFRIgG (lenercept), sIL-1RI, sIL-1RII, and sIL-6R), anti-inflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, human recombinant, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/ acetaminophen, olopatadine HCl, misoprostol, naproxen sodium, omeprazole, cyclophosphamide, rituximab, IL-1 TRAP, MRA, CTLA4-IG, IL-18 BP, anti-IL-18, anti-IL15, BIRB-796, SCIO-469, VX-702, AMG-548, VX-740, Roflumilast, IC-485, CDC-801, and Mesopram.

Non-limiting examples of therapeutic agents for cancers with which a peptide of the invention can be co-administered or used in combination include the following: budenoside; epidermal growth factor; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1.beta. monoclonal antibodies; anti-IL-6 monoclonal antibodies; growth factors; elastase inhibitors; pyridinyl-imidazole compounds; and antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90, or their ligands.

Other examples of therapeutic agents with which a peptide of the invention can be combined include the following: TNF antagonists, for example, anti-TNF antibodies, D2E7 (PCT Publication No. WO 97/29131), CA2, CDP 571, TNFR-Ig constructs (p75TNFRIgG and p55TNFRIgG (lenercept)), and PDE4 inhibitors. Binding proteins of the invention can be combined with, e.g., mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/ apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone HCl/ acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/ apap, colesevelam HCl, cyanocobalamin, folic acid, levofloxacin, methylprednisolone, natalizumab, and interferon-gamma.

Non-limiting examples of therapeutic agents with which a binding protein of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, and bisoprolol fumarate.

The pharmaceutical compositions of the invention may include a "therapeutically effective amount" or a "prophylactically effective amount" of a binding protein of the invention. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the binding protein are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a peptide of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Peptide-drug conjugates (PDCs) are targeted drug delivery systems, which combine the targeting specificity of a peptide (similar to that of the antibody in an ADC) with the cytotoxicity of a drug (or toxin). PDCs generally comprise a targeting peptide (which will be referred to in the discussion that follows simply as "peptide") covalently bound (conjugated) via a linker to a cytotoxic drug or toxin. The choice of specific peptide, linker and drug in each PDC, in combination, determines that PDC's targeting capability (specificity, binding affinity, etc.), pharmacokinetics, and mechanism of cell killing.

The term "peptide-drug conjugate" refers to poly- or oligo-amino acids having a specific sequence, such as an antibody mimic peptide, chemically linked to a chemical moiety, such as a therapeutic or cytotoxic agent (also referred as a substance). The term "agent" is used herein to denote a chemical compound, a mixture of chemical compounds, a biological macromolecule, or an extract made from biological materials. Preferably, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, maytansine, auristatins, puromycin and analogs or homologs thereof.

It is of utmost importance that the peptide specifically binds the desired target and with high affinity. Generally, the higher the binding affinity of the peptide, the more effective is the drug conjugate. As with ADCs, the choice of peptide-drug linker and its optimization also play an important role in the design of PDCs. At least two important aspects must be considered in designing a PDC linker. First, the linker should be capable of linking both the peptide and the drug without adversely affecting properties and activities of either; i.e., targeting functionality of the peptide and cytotoxic effects of the drug. Second, the linker should be stable during storage and in the systemic circulation until it reaches the target. Additionally, if a cleavable linker is used, the linker should be relatively easily cleaved (or otherwise permit separation of peptide and drug) after reaching the target cell.

Both cleavable and non-cleavable linkers can be used in conjugating peptides to drugs. Cleavable linkers can be cleaved intracellularly or extracellularly, and non-cleavable linkers cannot easily be enzymatically or chemically cleaved, if at all. These non-cleavable linkers generally undergo complete degradation in the lysosome along with their associated peptides. Again like ADCs, described above, the most frequently used cleavable linkers are hydrazone and disulphide linkers. Drugs used in PDCs are generally the same as those in ADCs.

Peptides possess several advantages over antibodies/antibody fragments in targeted drug delivery systems, including ease of synthesis, better tolerance of a wider range of pH and temperature, and flexibility in chemical modification. Perhaps most importantly, due to the peptide's smaller size and molecular weight it facilitates higher cell uptake as compared to antibodies. Moreover, targeting peptides are generally less toxic and have lower immunogenic potential than antibodies or their fragments. For at least all of the foregoing reasons, peptides are ideal candidates as targeting agents.

The antibodies, antibody fragments, peptides and combinations thereof currently in use for targeting in ADC and/or PDC systems are designed and identified from conventional antibodies or through time-consuming screening techniques, such as phage, ribosome and mRNA display. The present disclosure, by contrast, presents synthetic peptides possessing the functionality of known antibodies, thus bypassing the lengthy development and screening techniques.

Each of the peptides of the present disclosure comprises a motif sequence. These motif sequences comprise amino acid residues corresponding to amino acids in the native antibody "knobs" which pack the epitope "sockets" at the antibody-epitope interface, as is known from the antibody-epitope crystal structure. For a description of the knob-socket model, see H. Joo et al., *J. Molec. Biol.* (2012) 419:234-254, which is incorporated herein by reference for its teachings of the knob-socket model. Briefly, the knob-socket model describes contacts in the "packing" of peptide α-helices as a "knob" of one amino acid residue of a first α-helix, which fits into a "socket" of three amino acid residues of a second α-helix. Schematic diagrams of knob and socket packing interface lattices are shown in FIGS. 1B and 2, which represent the cetuximab-EGFR epitope interface, and a model mimic peptide-EGFR peptide interface, respectively. See also the Examples below. As shown in FIGS. 1B and 2, each epitope socket is packed by a particular knob, and is represented in a shade of gray. Each amino acid residue of the epitope socket is presented by its single-letter code within a circle along the solid black lines. The black lines represent covalent bonds between amino acids; socket residues which "pack" with their side chains are represented by a dashed black line; hydrogen bonds are represented by dashed red lines. The amino acid residues of the epitope socket not involved in packing are omitted or shown as a small gray dot in the diagram (without a letter code). The amino acids of the knobs are also within circles, inside the gray shaded regions.

The peptides described herein exhibit specificity, binding affinity and functionality equivalent to or better than that of the original/native antibodies, as demonstrated in the Examples below, based on the results of in vitro cellular binding/uptake and flow cytometry studies (specificity), surface plasmon resonance (SPR) studies (binding affinity), and phosphorylation studies (functionality—mimic peptide inhibition of phosphorylation).

The present disclosure also demonstrates effective incorporation of the peptides described herein in PDCs, which PDCs were synthesized, characterized and evaluated against various cell lines, as described in the Examples.

In some embodiments herein, peptides are described which particularly target EGFR or HER2. The overexpression of EGFR or HER2 has been implicated in the development of a wide range of epithelial cancers, including breast, colon, head and neck, kidney, pancreas and prostate. In certain embodiments, PDCs were synthesized comprising these peptides.

The compositions and methods described herein provide for peptides which are highly effective in mimicking native antibodies, while avoiding the limitations of using native antibodies such as time-consuming screening methods. The peptides disclosed herein can thus be used to target, treat, identify, bind, etc. a variety of targets such as, for example but without limitation, those implicated in the development of a wide range of epithelial cancers, including breast, colon, head and neck, kidney, pancreas and prostate cancers.

In some embodiment, the antibody mimic peptide can be used for diagnosing a disease. The disease is tumor or cancer. The disease is associated with abnormal expression of EGFR or HER2 proteins.

In one embodiment, the antibody mimic peptide further comprises a conjugate structure having a substance, wherein the substance is a detection reagent, such as a detector peptide labeled with a reporter moiety.

In one embodiment, the detector peptide is a peptide, or antigen-binding fragment thereof, that is specific for the EGFR or HER2 or PD1 or PDL1.

The reporter moiety can be any of a wide range of materials/reporter systems known in the art. In some embodiments, the reporter moiety comprises a first member of a ligand-receptor pair including, but not limited to, an enzyme (e.g., horseradish peroxidase (HRP), alkaline phosphatase, luciferase, beta.-galactosidase, glucose oxidase, lysozyme, malate dehydrogenase, glucose-6-phosphate dehydrogenase); metal sol, selenium sol, carbon sol, and the like; colored or colorable particles (e.g., colored or colorable latex particles); colloidal metal particles (e.g., colloidal gold, colloidal silver, colloidal platinum, colloidal selenium) and isotopes of radioactive and non-radioactive. Examples of methods known in the art for detecting the reporter include, but are not limited to, detection methods by visible inspection, ultraviolet (UV) and visible spectrophotometry, fluorimetry and radiation counters.

The reporter moiety may be covalently or non-covalently bound/coupled to the detector peptide. The binding/coupling can be accomplished by any method known in the art. For example, reagents used for binding/coupling include, but are not limited to, glutaraldehyde, p-toluene diisocyanate, various carbodiimide reagents, p-benzoquinone m-periodate, N,Ni-o-phenylenedimaleimide, recombinant methods, and the like.

EXAMPLES

In the following Examples, peptides specific for EGFR, HER2, PD1 and PDL1 were synthesized and characterized to determine their effectiveness especially as components of PDCs in targeted drug delivery.

Example Peptide Sequences for EGFR

Antibody mimics were designed utilizing the crystal structure of Cetuximab-EGFR and knob-socket model. The crystal structure (PDB 1YY9) was analyzed to determine the residues in Cetuximab which have maximum interaction with EGFR epitopes. The EGFR epitope surface was then analyzed and mapped to define sockets in which knobs from Cetuximab bind. Each socket is formed by three amino acid residues on the EGFR surface and binds with the amino acid knob residues from the antibody's complementary binding region loops. Antibody mimic molecules were designed by selecting the knob residues with high probability of packing into sockets on the EGFR surface.

Antibody mimics were designed by placing high-preference knob residues like Trp (W), Glu (E), Phe (F), Tyr (Y), and Ala (A) in the sockets, and were connected according to the distance between them with other amino acids. Twenty five antibody mimics (Pep1-Pep25) were designed having different knob residues based on the frequency in the VSS and ISI sockets. Antibody mimics with sequences, Pep1-Pep11 were designed using knobs YY, YW, YL, YI, YV, YF, WY, LY, IY, VY, FY respectively in VSS and ISI sockets. Pep12-Pep22 were designed in a similar way with an additional threonine residue. Knobs in Pep12-Pep22 have TYY, TYW, TYL, TYI, TYV, TYF, TWY, TLY, TIY, TVY, TFY respectively. Pep23 and Pep24 were designed to have the reverse sequence of Pep11 and Pep6 to test the sequence requirement for binding, and Pep25, a scrambled peptide, was created as a negative control.

Molecular modeling studies: The interactions between the original antibody/designed peptides and EGFR were identified by docking studies using Molecular Operating Environment (MOE) software. The antibody mimic molecules were prepared by adding protons and performing the stochastic confirmation approach to find the lowest energy confirmation. The molecules were then energetically minimized and docking was performed. Conformation of the antibody mimic with lowest energy was then analyzed by MOE software to determine the binding energy, which indicates better binding. The total number of interactions and preserved interactions between EGFR and designed molecules, which shows the similarly in binding of the designed peptide with the original antibody, were also analyzed. Antibody mimics having low binding energy and a higher number of interactions and preserved interactions were then selected for further experiments and evaluation.

Design of antibody mimics was developed based on the Cetuximab-EGFR crystal structure and Knob-Socket model. Using the frequency data of knobs and sockets, the design of peptide sequences was developed based on those knobs which best fit into the sockets presented on the EGFR epitope. A ribbon diagram of the interface and side-chains of the amino acids which form packing sockets are shown in FIG. 1A. C-alpha positions of the knobs from the antibody are represented as sphere. Orange color represents knobs from CDR1 (the bottom ball), purple for CDR2 (top three balls), and green for CDR3 amino acids (middle four balls).

Figure 23:
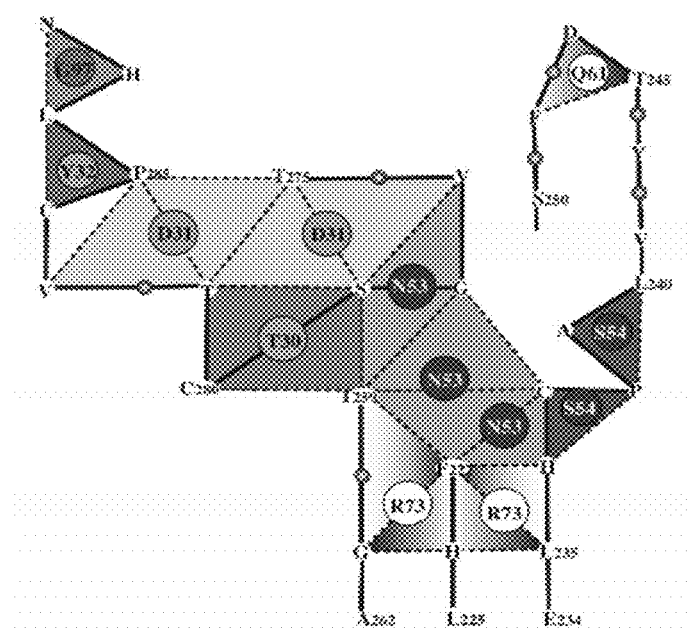
FIG. 23 shows a 2-D plot of the binding interface between pertuzumab and HER2 using the Knob-Socket model.

A schematic of the packing interface lattice represented by knobs and sockets is shown in FIGS. 1B, 2 and 23. Sockets packing the same knob are represented in the gray scale. Residues forming packing sockets are presented along the solid black line, and those which are not involved with packing are omitted or shown as small gray dots. Knobs are presented as circles, color-coded in the same way as in the ribbon diagram. Molecular modeling and mapping data suggested that the tyrosine 102 residue (Y102) is very important, as it showed multiple interactions. The Y102 residue was found to be a knob for the ISI, SVI, VAI, AFI, and AQF socket residues on EGFR.

The drug auristatin E, cetuximab, the peptide Pep11, and a Pep11-auristatin E PDC were studied and the $IC_{50}$ value of each molecule was obtained. For Pep11 see Table 1 (No. 11). As is known, cetuximab is a chimeric mouse/human monoclonal antibody (mAb) which binds the EGF receptor (EGFR), and is used; e.g., in cancer treatment. The studies were conducted using two cancer cell lines, A431 and MDA-MB-468, which overexpress EGFR, and a control cell line, HEK 293, which does not overexpress EGFR.

Peptides specifically bound and were internalized by EGFR overexpressing cell lines at levels three- to four-fold greater than control cells. Peptides showed receptor binding affinity (as provided by the calculated $K_D$, described below), in the nanomolar range, with Pep11 exhibiting a binding affinity of 252 nM as shown by surface plasmon resonance (SPR) studies. The results of EGFR phosphorylation studies also demonstrated that peptides binding to EGFR would inhibit EGF binding, at a level similar to that of cetuximab. The specificity, binding affinity, and functional activity of the peptides disclosed herein, as demonstrated in the Examples below, show that these peptides possess the important characteristics of the corresponding native antibodies.

The PDC was also shown to be approximately 10-fold more potent than the drug alone in its toxicity towards EGFR overexpressed cancer cells. The PDC also demonstrated a potency more than 100-fold lower than drug alone in toxicity against control cells.

A ribbon diagram of the cetuximab-EGFR binding interface and side-chains of the amino acids which form packing sockets in the epitope is shown in FIG. 1A. The C-alpha positions of the antibody sequence knobs are represented in FIG. 1A as the spheres, each corresponding to a knob sequence from cetuximab's complementarity determining regions 1, 2 and 3, as shown. In FIG. 1B, the knob amino acids are numbered according to their position in the cetuximab sequence, and color coded to correspond to the CDRs shown in the ribbon diagram of FIG. 1A. FIG. 2 illustrates the same epitope sockets with the knobs from a peptide.

Twenty-five peptides (Pep1-Pep25; see Table 1) were synthesized, with different knob residues associated with the VSS and ISI sockets of the EGFR epitope. See FIG. 1B, in which the VSS socket is packed, where "VSS" and "ISI" refer to the three amino acids primarily forming the sockets (i.e., valine-serine-serine and isoleucine-serine-isoleucine, respectively; see FIGS. 1a and 2). The amino acid sequences represented by Pep1-Pep11 have knob residues YY, YW, YL, YI, YV, YF, WY, LY, IY, VY, and FY, respectively, which fit in the VSS and ISI sockets.

Pep12-Pep22 have an additional threonine residue (Thr or T) relative to Pep1-Pep11. Pep12-Pep22 therefore have sequences TYY, TYW, TYL, TYI, TYV, TYF, TWY, TLY, TIY, TVY, and TFY, respectively, as knob residues. Pep23 and Pep24 have the reverse sequence of Pep11 and Pep6, respectively. A peptide of scrambled, random sequence was also created, Pep25, as a negative control.

For example, Pep6, Pep11, Pep22, and Pep24 demonstrated a calculated binding energy in the range of −32 kcal/mol to −41 kcal/mol, and high number of calculated total and preserved interactions with the EGFR epitope (in the range of 13-17 total and 4-8 preserved interactions). By comparison Pep25, the control peptide of scrambled sequence, had a calculated docking energy of −23.69 kcal/mol, 7 total interactions with the epitope and 2 preserved interactions. Molecular binding studies between the peptides and EGFR indicated that the total number of interactions and preserved interactions between EGFR and the peptides demonstrate the similarity of peptide-epitope binding with that of native antibody as shown in Table 3.

TABLE 1

Peptide sequences

| No. | Molecule | Energy (kcal/mol) | Total Interactions | Preserved Interactions |
| --- | --- | --- | --- | --- |
| 1. | WSGENGPGYYDYEA (SEQ ID NO: 1) | −35.80 | 13 | 7 |
| 2. | WSGENGPGYWDYEA (SEQ ID NO: 2) | −24.54 | 13 | 6 |
| 3. | WSGENGPGYLDYEA (SEQ ID NO: 3) | −33.82 | 13 | 5 |
| 4. | WSGENGPGYIDYEA (SEQ ID NO: 4) | −28.95 | 13 | 7 |
| 5. | WSGENGPGYVDYEA (SEQ ID NO: 5) | −28.42 | 13 | 3 |
| 6. | WSGENGPGYFDYEA (SEQ ID NO: 6) | −32.47 | 13 | 4 |
| 7. | WSGENGPGWYDYEA (SEQ ID NO: 7) | −35.91 | 13 | 4 |
| 8. | WSGENGPGLYDYEA (SEQ ID NO: 8) | −28.28 | 14 | 4 |
| 9. | WSGENGPGIYDYEA (SEQ ID NO: 9) | −26.00 | 14 | 3 |
| 10. | WSGENGPGVYDYEA (SEQ ID NO: 10) | −28.39 | 13 | 6 |
| 11. | WSGENGPGFYDYEA (SEQ ID NO: 11) | −40.43 | 17 | 8 |
| 12. | WSGENGPGTYYDYEA (SEQ ID NO: 12) | −31.28 | 14 | 6 |
| 13. | WSGENGPGTYWDYEA (SEQ ID NO: 13) | −28.78 | 12 | 4 |
| 14. | WSGENGPGTYLDYEA (SEQ ID NO: 14) | −35.62 | 14 | 5 |
| 15. | WSGENGPGTYIDYEA (SEQ ID NO: 15) | −31.25 | 10 | 2 |
| 16. | WSGENGPGTYVDYEA (SEQ ID NO: 16) | −34.33 | 13 | 2 |
| 17. | WSGENGPGTYFDYEA (SEQ ID NO: 17) | −37.13 | 13 | 6 |
| 18. | WSGENGPGTWYDYEA (SEQ ID NO: 18) | −37.94 | 13 | 7 |
| 19. | WSGENGPGTLYDYEA (SEQ ID NO: 19) | −31.89 | 14 | 7 |
| 20. | WSGENGPGTIYDYEA (SEQ ID NO: 20) | −29.32 | 12 | 4 |
| 21. | WSGENGPGTVYDYEA (SEQ ID NO: 21) | −36.50 | 14 | 6 |
| 22 | WSGENGPGTFYDYEA (SEQ ID NO: 22) | −35.34 | 14 | 6 |
| 23 | AEYDYFGPGNEGSW (SEQ ID NO: 23) | −30.92 | 10 | 3 |

TABLE 1-continued

Peptide sequences

| No. | Molecule | Energy (kcal/mol) | Total Interactions | Preserved Interactions |
|---|---|---|---|---|
| 24 | AEYDFYGPGNEGSW (SEQ ID NO: 24) | −40.31 | 13 | 4 |
| 25. Control | SGEWAYDGYEPNFG (SEQ ID NO: 25) | −23.69 | 7 | 2 |

Figure 3:
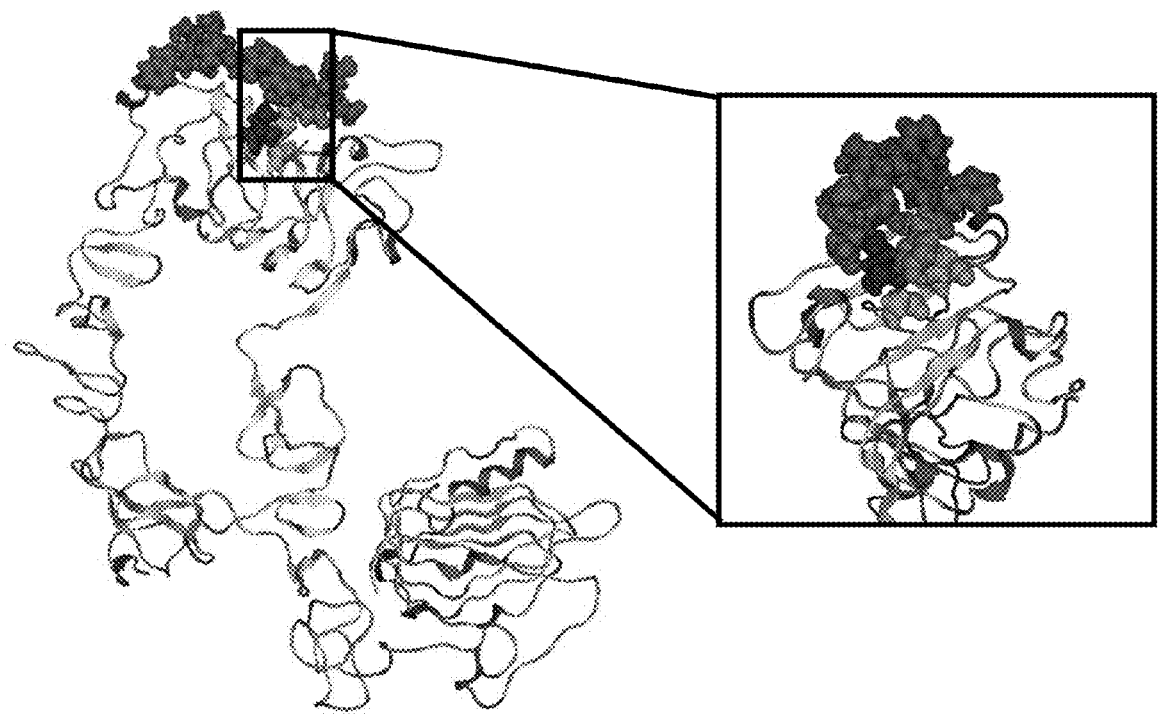
FIG. 3 shows a docking image of the Pep11 mimic peptide in EGFR.

In FIG. 3, Pep11 is illustrated docking at the same site in EGFR as cetuximab. Tyrosine residue (pink) from Pep11 is representing a knob which is fitting into the socket formed by alanine (orange), valine (green) and isoleucine (blue) in the EGFR epitope.

Binding Specificity Studies of Peptides

A431, MDA-MB-468 and HEK 293 cells were cultured in 75 cm$^2$ culture flasks in DMEM supplemented with 10% FBS. For binding/internalization studies, 5×10$^5$ cells were seeded in cover slips in 6 well culture plates overnight. After the medium was removed, the cells were washed with HBSS and then cells were treated with FITC labeled antibody mimic and scrambled (control) peptide in serum free DMEM for 30 minutes at 37° C. Cells were then washed with HBSS to remove any unbound peptides and incubated with AlexaFluor 594 wheat germ agglutinin to stain cell membranes. Cells were fixed with 4% paraformaldehyde and cover slips were mounted on slides which contain a drop of SlowFade®. Cells were then imaged with an inverted Leica DMIRE2 fluorescence microscope (Leica Biosystems Richmond Inc., Richmond, USA) using a Yokogawa CSUX1 confocal scanner unit. For flow cytometry studies, cells were washed with HBSS after incubation with antibody mimics, control peptide for 30 minutes, and dissociated using trypsin-EDTA. Cells were then centrifuged at 500 g for 5 min. Supernatant was removed and cell pellets were re-suspended in FACS solution. The cell suspension was then analyzed on a Beckman Coulter flow cytometer and data were analyzed using the Cell Questpro. A total of 10000 events were collected monitoring FITC.

Binding Affinity Studies of Peptides

Binding affinity constant of antibody mimics was calculated by surface plasmon resonance (Reichert SR7000DC). A carboxymethyl dextran gold sensor chip was activated by N-hydroxysuccinimide (NHS) and N-ethyl-N"-[3-(diethylamino)propyl] carbodiimide (EDC) at 25° C. using phosphate buffered saline pH 7.4 with 0.05% tween 20 as running buffer. Recombinant human EGFR (30 μg/mL), or BSA (20 μg/mL) as control, was immobilized by flowing the antigen over the activated chip in 10 mM sodium acetate buffer pH 4.5 at 15 μL/min. for 6 minutes. Unreactive sites were blocked by flowing over the chip 1 M ethanolamine pH 8.5 at 10 μL/min for 8 minutes. The real-time binding and dissociation rates of different concentrations of mimic peptides over EGFR and BSA were studied by flowing the peptides over the chip at 25 μL/min. The resulting sensograms were globally fitted using Scrubber2 software (Bio-Logic Software, Campbell, Australia) in a 1:1 binding model to determine the association rate ($k_{on}$), dissociation rate ($k_d$ or $k_{off}$), and dissociation constant $K_D$.

EGFR Phosphorylation Studies of Peptides

Cell based ELISA was performed to determine the inhibition of EGFR phosphorylation. Briefly, 2×10$^4$ A431 cells were seeded in 96 well plates in DMEM medium supplemented with 10% FBS for 24 hours. The cells were then treated with different peptides and cetuximab 10 μM in serum free medium for 45 minutes at 37° C. After that, cells were stimulated by EGF 50 ng/mL for 20 minutes at 37° C. After washing the cells, fixing solution was added for 20 minutes at room temperature. Cells were treated with Primary mouse anti EGFR and anti phospho EGFR antibodies were added first, after washing cells were treated with anti-mouse HRP secondary antibody for 1 hour at room temperature. Phosphorylation inhibition was calculated using determined as follows:

$$\frac{(OD \text{ Untreated}) - (OD \text{ Treated})}{(OD \text{ Untreated})} * 100$$

Figure 4:
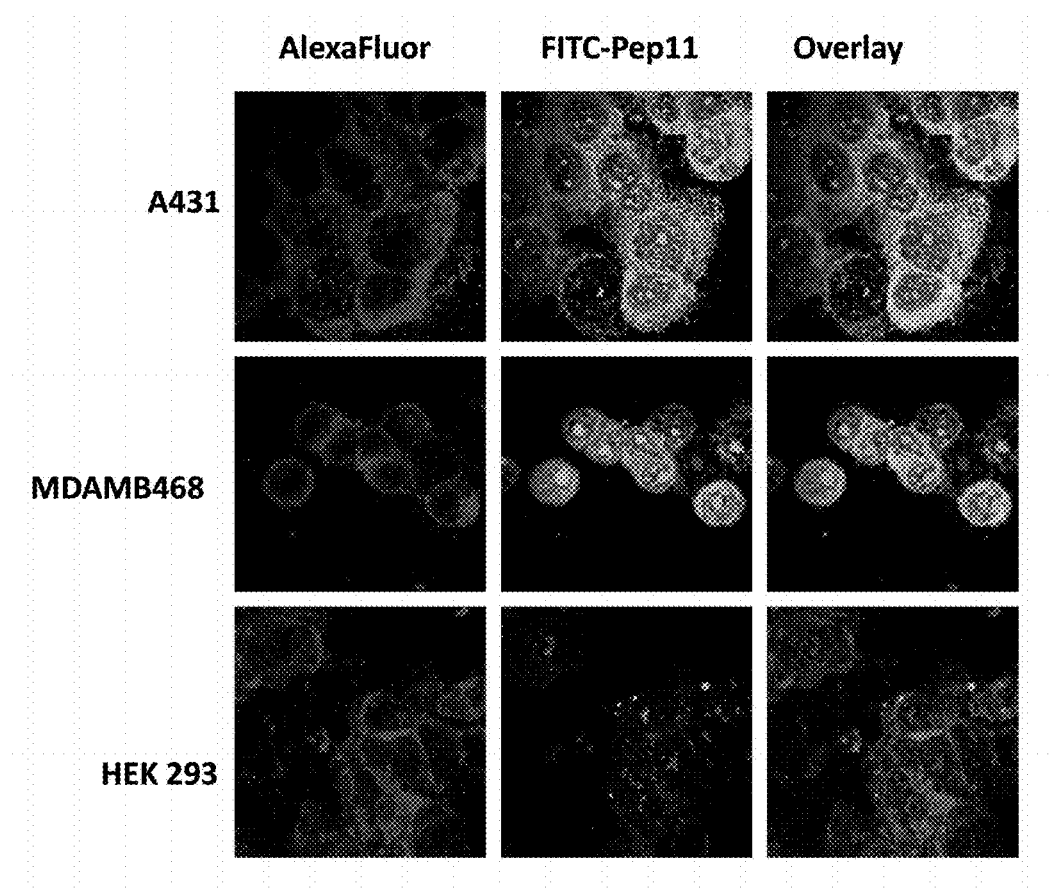
FIG. 4 shows confocal images of treated cells of cell lines A431, MDA-MB-468 and HEK 293. The AlexaFluor column represents cells treated with only membrane dye, FITC-Pep11 displays cells treated with FITC-conjugated Pep11 peptide, and Overlay represents a merge of the AlexaFluor and FITC-PEP11 images.
Figure 5:
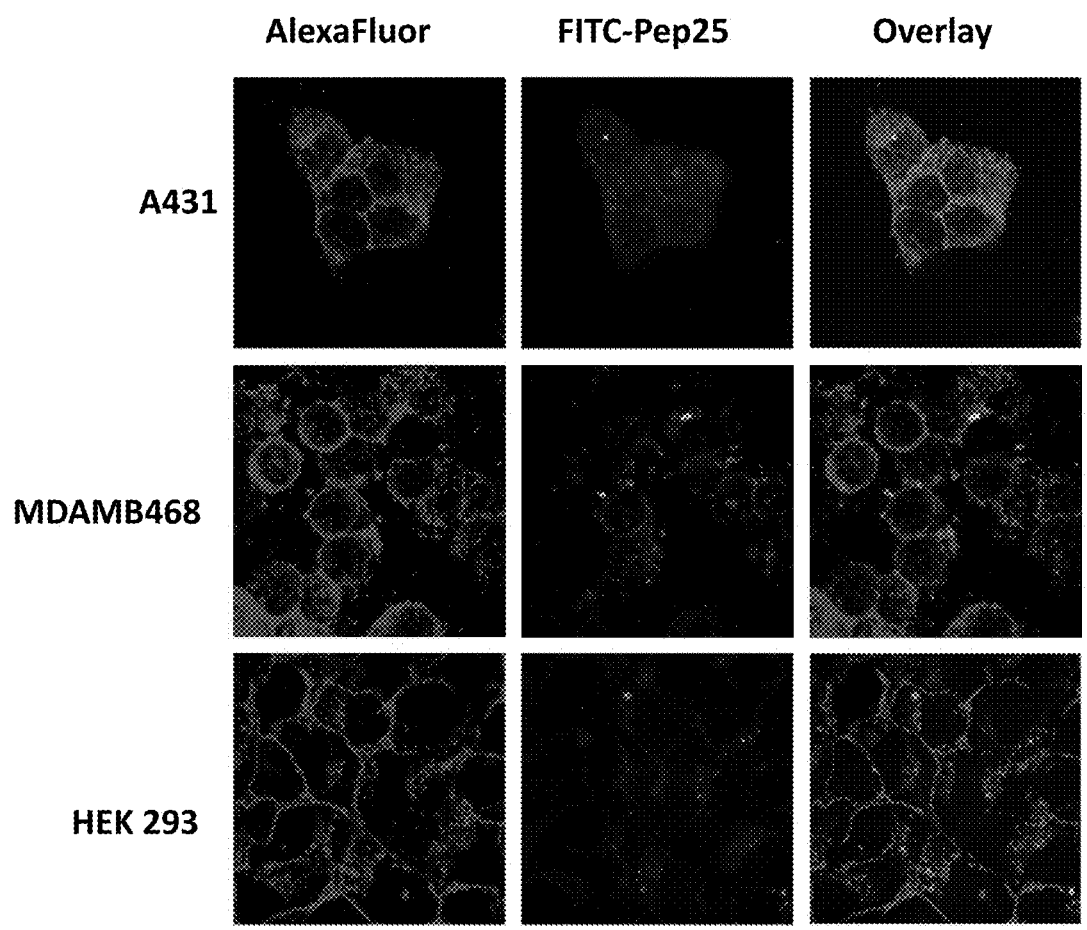
FIG. 5 shows confocal images of treated cells of cell lines A431, MDA-MB-468 and HEK 293. The AlexaFluor column represents cells treated with only membrane dye; FITC-Pep25 displays the cells treated with FITC-conjugated peptide Pep25, the scrambled peptide; and, Overlay column represent a merge of the AlexaFluor and FITC-Pep25 images.

In the present Examples, FITC-labeled peptides specifically bound the cell membranes and were internalized into the cells which overexpress EGFR within 30 minutes when incubated at 37° C. As observed from the images (see FIGS. 4 and 5), significantly higher fluorescence was seen in A431 and MDA-MB-468 cell lines as compared with HEK 293 cells, which demonstrated the binding specificity of the peptides towards EGFR. The scrambled antibody mimic (Pep25) showed negligible binding to the cell line overexpressing EGFR demonstrating the specificity for EGFR of the peptides disclosed herein.

Figure 6:
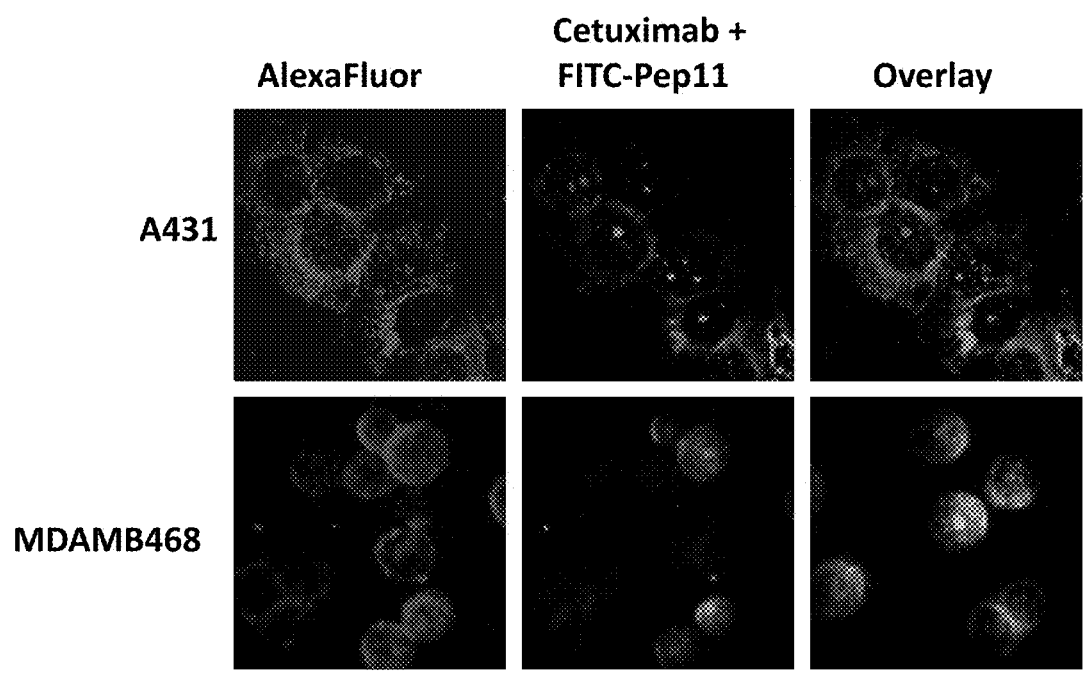
FIG. 6 shows confocal images of treated cells from cell lines A431 and MDA-MB-468, demonstrating treatment with Pep11 after treatment with cetuximab. The AlexaFluor column represents cells treated with only membrane dye; cetuximab+FITC-Pep11 displays cells treated with FITC-conjugated peptide Pep11 after blocking the EGFR by cetuximab for 30 min.; and, Overlay represents a merge of the AlexaFluor and cetuximab+FITC-Pep11 images.

Epitope specificity of the peptides was evaluated by cellular uptake of the peptides, as an example cells treated with Pep11 for 30 minutes at 37° C. and fluorescence images with cetuximab than from those not pre-incubated with antibody were determined. As shown in FIG. 6, the results demonstrated that cell receptors were blocked by cetuximab in the pre-incubated cells and that binding of Pep11 to cells was inhibited/decreased following cetuximab treatment.

Figure 7:
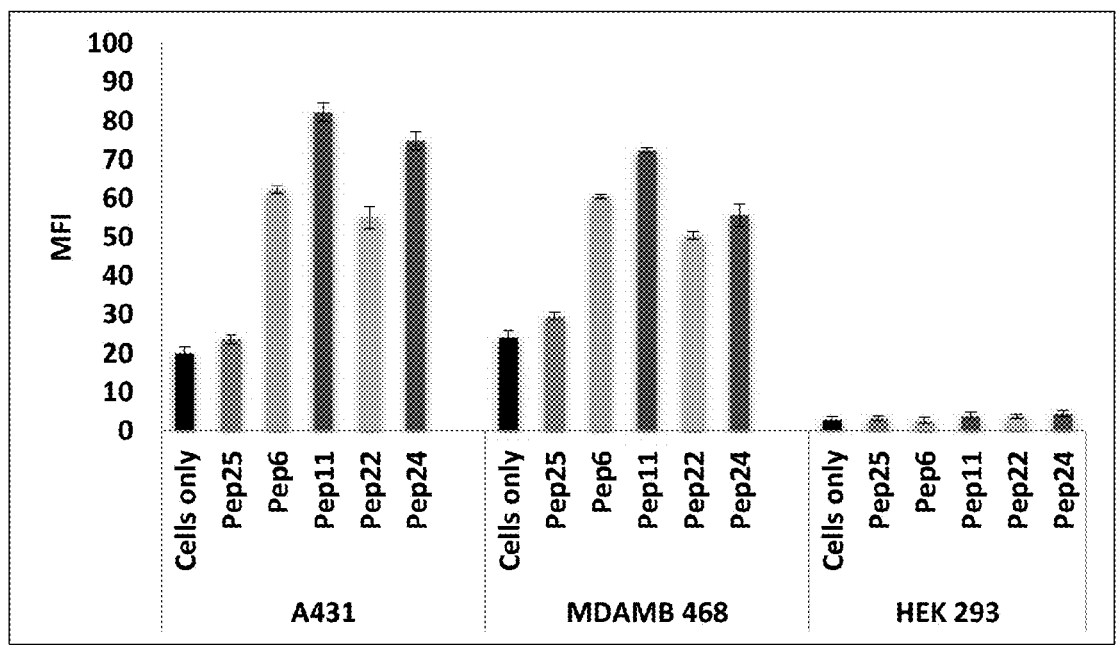
FIG. 7 shows flow cytometry results displaying the mean fluorescent intensity (MFI) of cells from cell lines A431, MDA-MB-468 and HEK 293, treated with different mimic peptides (as listed) or untreated ("Cells only").

Binding specificity of peptides was also studied using flow cytometry. In this study, the binding specificity was verified by differential cellular uptake of peptide by cells with different levels of EGFR expression. Internalization of peptides was significantly higher in cancer cell line A431 and MDA-MB-468, which overexpress EGFR, as depicted by the increase in mean fluorescence intensity (MFI). See FIG. 7. The uptake of the peptides was most likely a result of receptor mediated endocytosis. Negligible uptake of the peptides was observed in the FMK 293 cell line, which does not overexpress EGFR, when compared to the fluorescent intensity of cell only samples. These results demonstrated the specificity of the peptides towards EGFR. The scrambled peptide (Pep25) showed negligible binding to the cancer cell lines, which demonstrated the specificity of the non-scrambled peptides. All the peptides (non-scrambled) showed a 3- to 4-fold increase in fluorescent intensity as compared with the control ("Cells only").

Figure 8A:
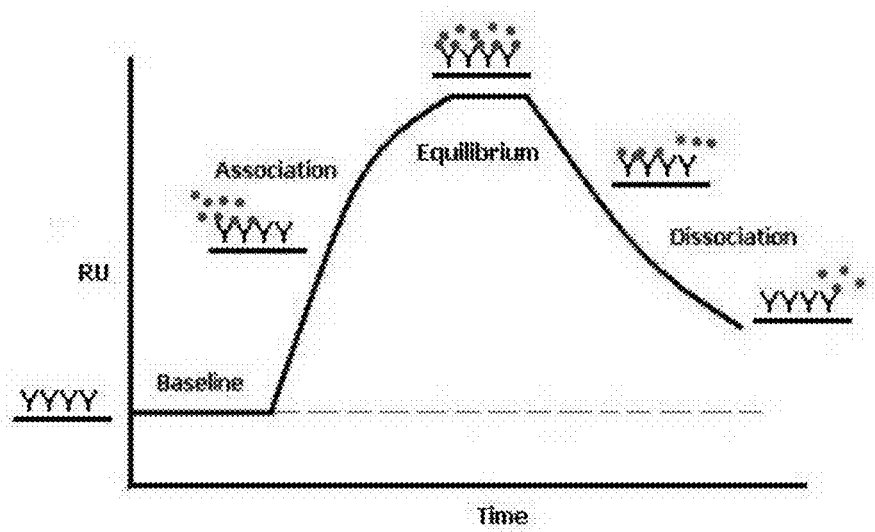
FIG. 8A shows a typical surface plasmon resonance (SPR) sensogram.

Antibody binds to its target antigen not only with specificity, but also with high affinity. Binding affinity indicates how quickly and with what strength the antibody/mimic hinds the target antigen. Binding affinity of any antibody/mimic for target can be determined by SPR analysis. This results in a sensogram, as shown in FIG. 8a, which is a typical sensogram (where "YYYY" is immobilized antigen), which has an association, equilibrium and dissociation phase. In the association phase the antibody/mimic analyte begins binding (associating with) the immobilized antigen and thus producing measurable SPR response, until binding reaches equilibrium. At equilibrium, the number of binding sites becomes saturated and binding of antibody/mimic to antigen stops, until a dissociation phase is observed where antibody/mimic begins to dissociate from antigen.

Figure 8B:
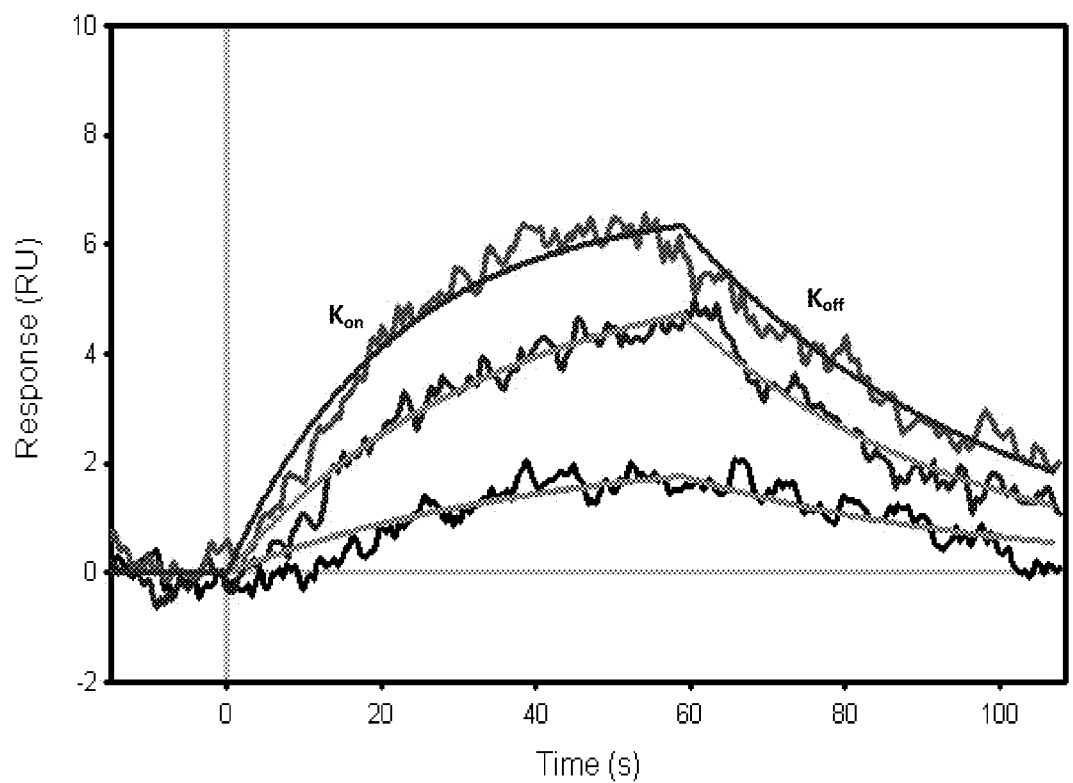
FIG. 8B shows sensogram results of surface-immobilized EGFR treated with Pep11 (RU=resonance units; s=seconds).
Figure 9:
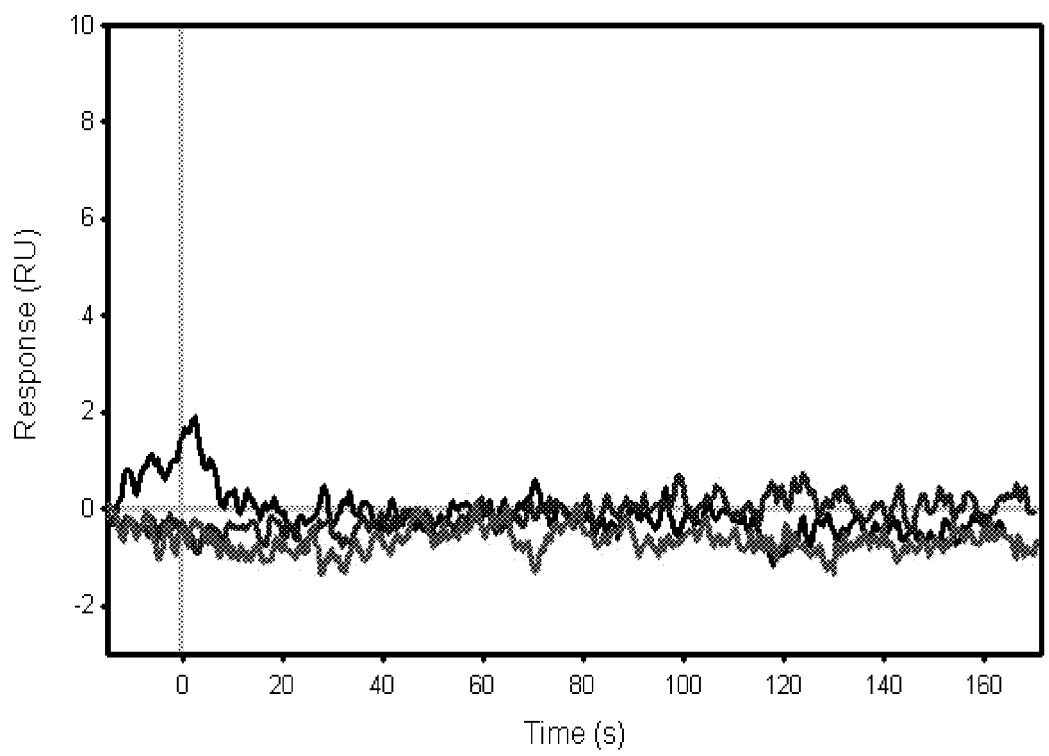
FIG. 9 shows sensogram results of surface-immobilized bovine serum albumen (BSA) treated with scrambled peptide, Pep25.
Figure 10:
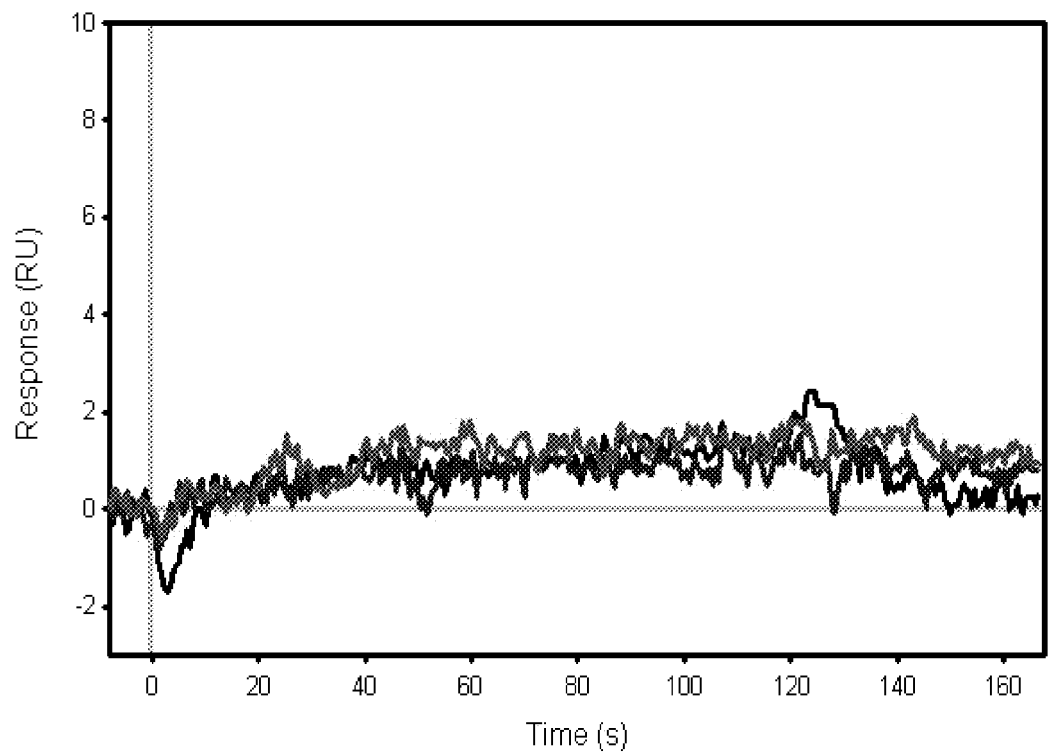
FIG. 10 shows SPR sensogram results of surface-immobilized EGFR treated with scrambled peptide, Pep25.
Figure 11:
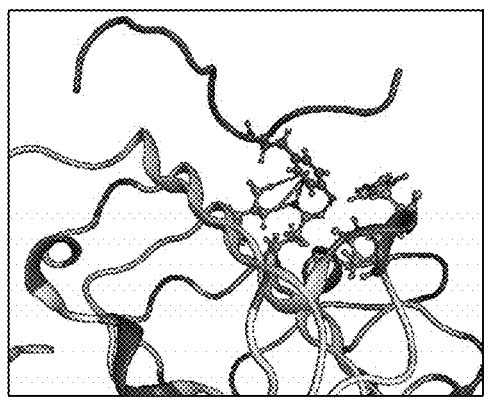
FIG. 11 shows the interaction of the first tyrosine residue in Pep11 with EFGR (A), and the interaction of the first tyrosine residue in Pep22 with EGFR (B).
Figure 11:
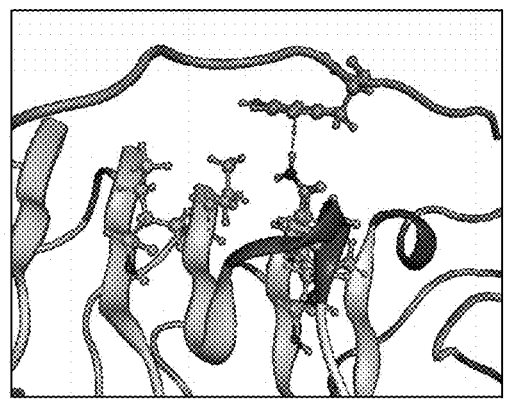

Binding affinity constants, as represented by $K_D$ (M), were obtained by SPR analysis of peptides with EGFR by the methods described above, and were in the range of 252 nM-4.7 μM. See Table 2, below. The sensograms showed concentration-dependent binding, with an increase in binding corresponding to an increase in mimic peptide concentration. See FIG. 8b (where the curves represent various concentrations of Pep11). Antibody mimics with $K_D$ values in the range of 23-800 nM are reported in the literature. Binding affinity of previous antibody mimics have been 20- to 200-fold lower than the affinity of the original antibody. By contrast, peptides in the present Example demonstrated a binding affinity ($K_D$) for EGFR approximately 50-fold greater than cetuximab's (e.g., 252 nM for Pep11 vs. 5.2 nm for cetuximab). These results clearly demonstrated that the peptides of the present disclosure are have high affinity for EGFR, and will thus be very effective and useful as targeting moieties for EGFR.

Scrambled peptide did not show binding to the EGFR and no increase in response was seen with increase in concentration of the control peptide. This shows the specificity of the [non-scrambled] peptides. That scrambled peptide did not bind to EGFR could be attributed to the fact that in scrambled peptide the packing of knob and socket pairs is disturbed, and designed knobs can no longer pack into their respective sockets. Moreover, [non-scrambled] peptides did not show binding to BSA, thus demonstrating the selectivity and specificity of these peptides towards EGFR.

Pep24, having the reverse amino acid sequence of Pep6, still demonstrated binding affinity similar to that of Pep6 with comparable $K_D$ values, thus demonstrating that the peptide confirmation remains the same as that of Pep6, even with reverse amino acid sequence.

Figure 13:
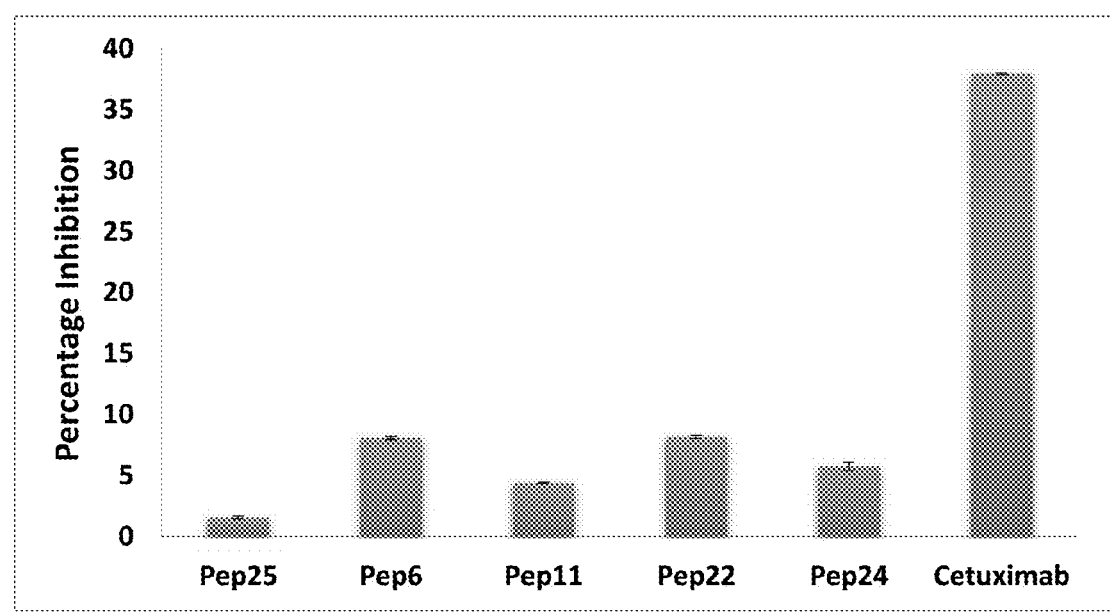
FIG. 13 shows the percentage of inhibition of phosphorylation by different antibody mimic peptides and cetuximab after stimulation of cells by 50 ng/ml EGF.

The percent inhibition by peptides was around 5-fold less than that of cetuximab (see FIG. 13), which could be attributed to the small size of the peptides—though these molecules bind to the same site as that of cetuximab, they may not be able to prevent a conformational change as cetuximab does, which conformational change would inhibit the ligand from binding to EGFR.

Synthesis of Peptide Drug Conjugates

The following Example demonstrates a peptide as described herein conjugated to a drug to create a mimic PDC. In the following Example auristatin E (AE) is the drug. Auristatin E is a known anti-neoplastic agent, and when used for treatment, for example of cancer, is bound to antibody.

Synthesis of 5-Benzoylpentanoic Ester of Auristatin E

Figure 14:
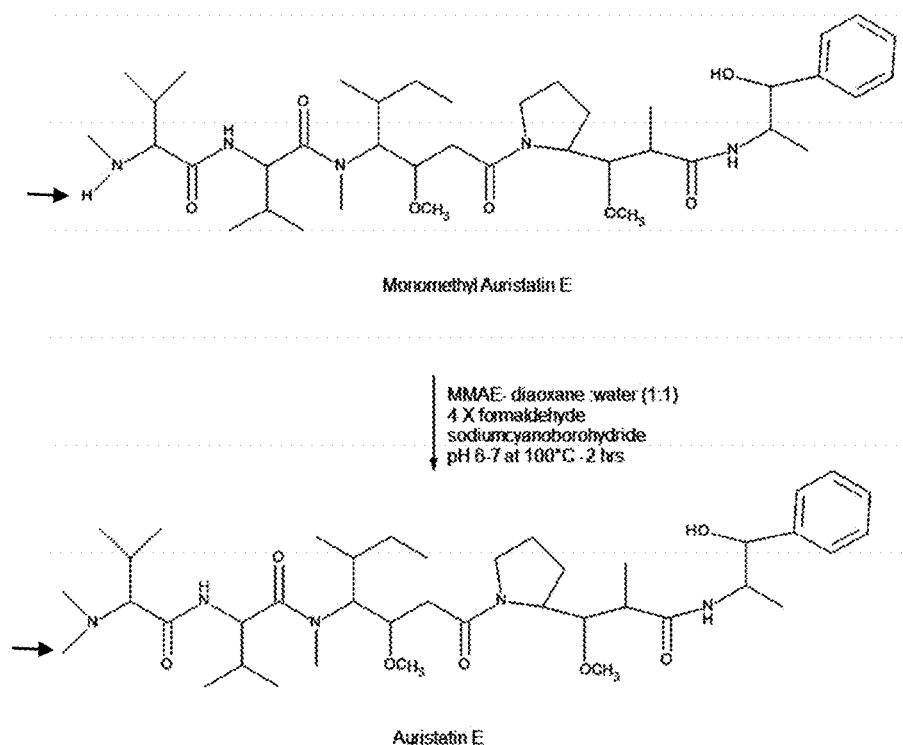
FIG. 14 shows synthesis of auristatin E.

Monomethyl auristatin E (MMAE) was dissolved in dioxane:water (1:1) to create a drug solution, and 0.42 mmol of 37% aqueous formaldehyde and 0.13 mmol of sodium cyanobohydride were added to the drug solution. The pH was adjusted to 6-7 with 0.1 N HCl and the mixture was heated at 100° C. for 2 hours. The reaction mixture was then poured into a saturated sodium bicarbonate aqueous solution and ethyl acetate. Ethyl acetate layer was separated and dried by adding sodium sulphate. A white crystal powder was obtained. See FIG. 14.

Figure 15:
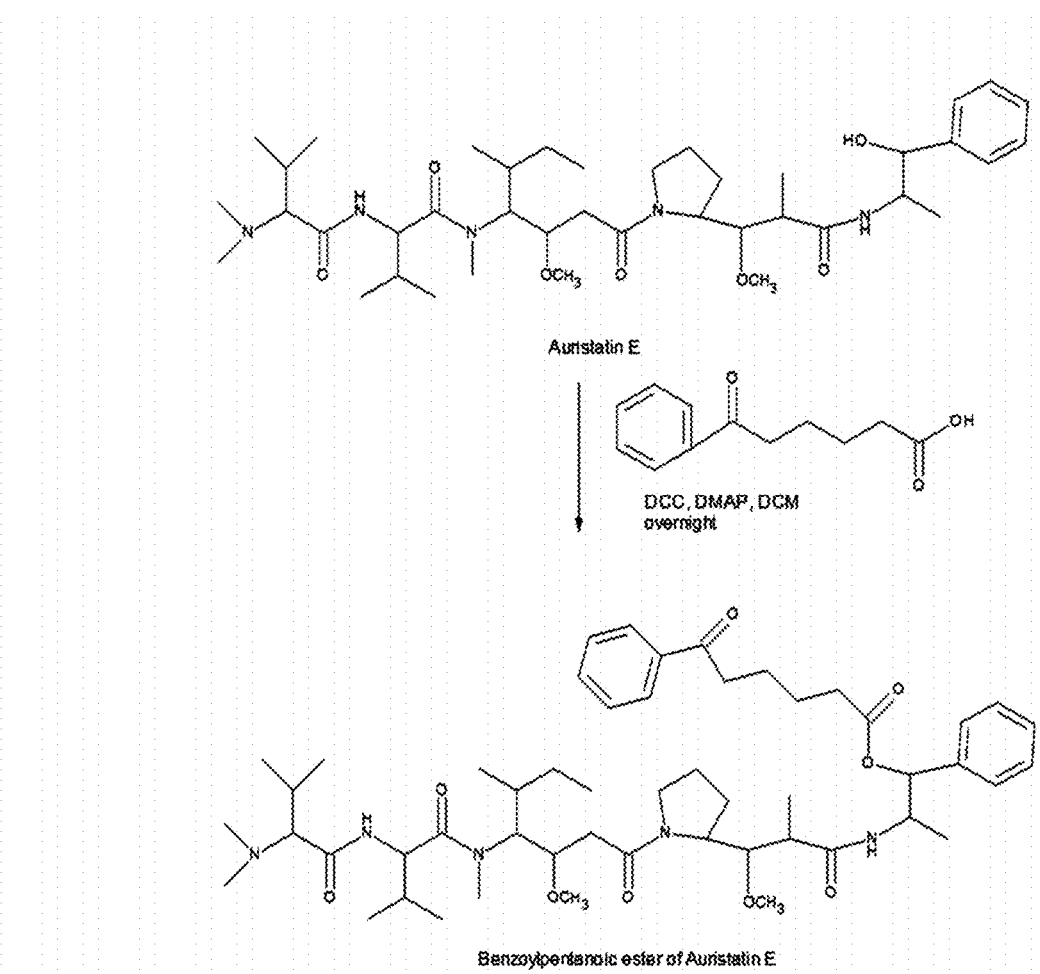
FIG. 15 shows synthesis of 5-benzoylpentanoic ester of auristatin E (BPA).

Auristatin E (0.07 mmol) was dissolved in anhydrous methylene chloride (DCM), followed by the addition of 0.14 mmol N,N'-Dicyclohexylcarbodiimide (DCC) and 4-Dimethylaminopyridine (DMAP). Then, 5-benzoylpentanoic acid (0.14 mmol) was added to the auristatin E solution. The reaction was performed overnight at room temperature. The product was purified and separated using preparative thin layer chromatography using 5% methanol in ethyl acetate as developing solvent. See FIG. 15.

Synthesis of Hydrazone Intermediate

Benzoylpentanoic ester of auristatin E (1 eq) and maleimidocaproyl hydrazide (5 eq) were added together in

TABLE 2

| SPR results on EGFR as immobilized surface | | | |
|---|---|---|---|
| Peptide | Kon $M^{-1}s^{-1}$ | Koff $s^{-1}$ | KD M |
| Pep6 | $1.21 * 10^3 \pm 0.01 * 10^3$ | $5.81 * 10^{-3} \pm 0.03 * 10^{-3}$ | $4.80 * 10^{-6} \pm 0.25 * 10^{-6}$ |
| Pep11 | $1.00 * 10^5 \pm 0.03 * 10^5$ | $2.52 * 10^{-2} \pm 0.05 * 10^{-2}$ | $2.52 * 10^{-7} \pm 0.09 * 10^{-7}$ |
| Pep22 | $4.35 * 10^4 \pm 0.02 * 10^4$ | $2.59 * 10^{-2} \pm 0.04 * 10^{-2}$ | $5.95 * 10^{-7} \pm 0.10 * 10^{-7}$ |
| Pep24 | $1.43 * 10^4 \pm 0.01 * 10^4$ | $1.03 * 10^{-1} \pm 0.03 * 10^{-1}$ | $7.20 * 10^{-6} \pm 0.32 * 10^{-6}$ |
| Pep25 | NA | NA | NA |

TABLE 3

| Knob-socket frequency of binding for ISI socket | | | | | | | | | | | | | | | | | |
|---|---|---|---|---|---|---|---|---|---|---|---|---|---|---|---|---|---|
| Knobs | W | P | G | Y | F | V | I | L | A | E | K | R | Q | D | S | T | N | M | H | C |
| Frequency | 0 | 1 | 1 | 7 | 0 | 3 | 2 | 1 | 2 | 2 | 1 | 0 | 4 | 0 | 1 | 3 | 4 | 2 | 2 | 0 |

Figure 12:
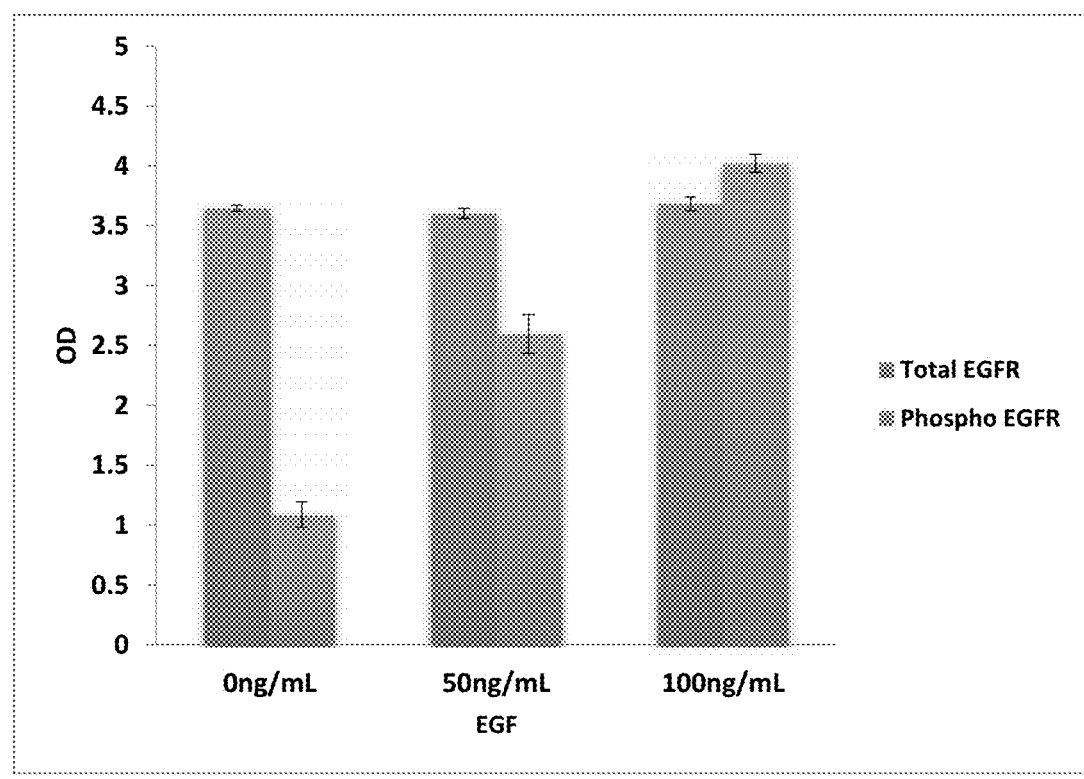
FIG. 12 shows the optical density (OD) for total and phosphorylated EGFR at varying concentrations, as analyzed by ELISA.
Figure 16:
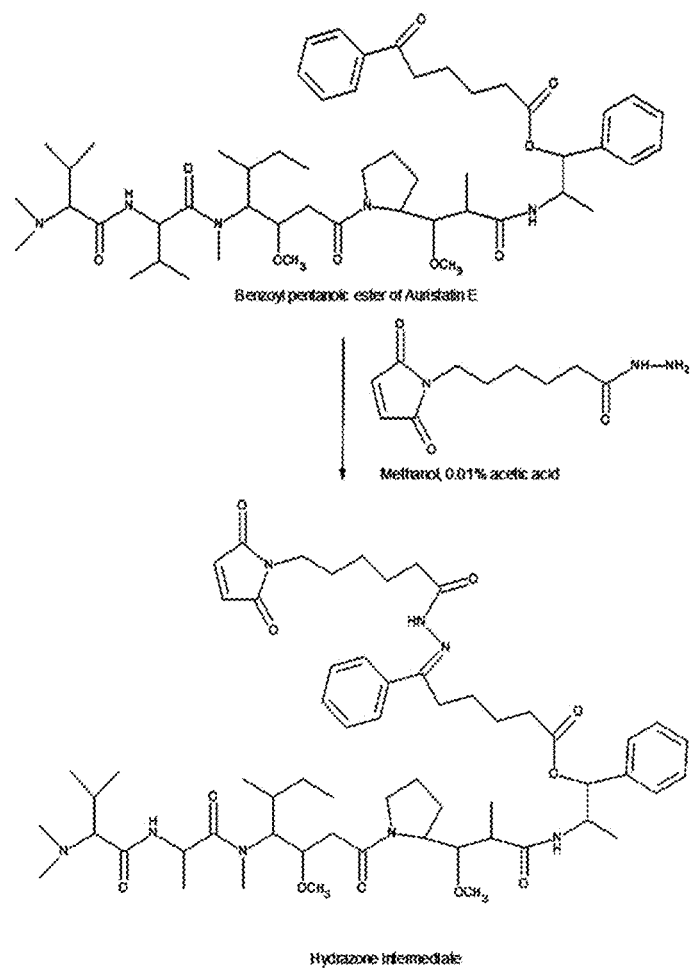
FIG. 16 shows synthesis of a hydrazone intermediate.

In the EGFR phosphorylation study, A431 cells, which overexpress EGFR, were used. Phosphorylation caused by the different peptides and cetuximab was determined by cell-based ELISA. Total EGFR protein content and phosphorylated EGFR were both were calculated. Total EGFR content remained the same with and without stimulation by EGF at 50 ng/mL when anti-EGFR antibody was used as the primary antibody. EGF stimulation did not increase the total EGFR content, but only caused an increase in phosphorylated EGFR. Anti-phosphorylated EGFR antibody depicted the percent inhibition of phosphorylation by different molecules and was in the range of 4.40-8.13% as compared with 38% by cetuximab when stimulated by EGF. See FIG. 12.

anhydrous methanol with 0.01% acetic acid. The reaction mixture was stirred overnight at room temperature. The reaction mixture was added into DMSO and only methanol was evaporated under reduced pressure. Finally, the product was purified using a semi-preparative column in reversed-phase (RP) HPLC using a gradient of triethylammonium acetate buffer pH 7 and acetonitrile. See FIG. 16.

Synthesis of Peptide Drug Conjugate

Figure 17:
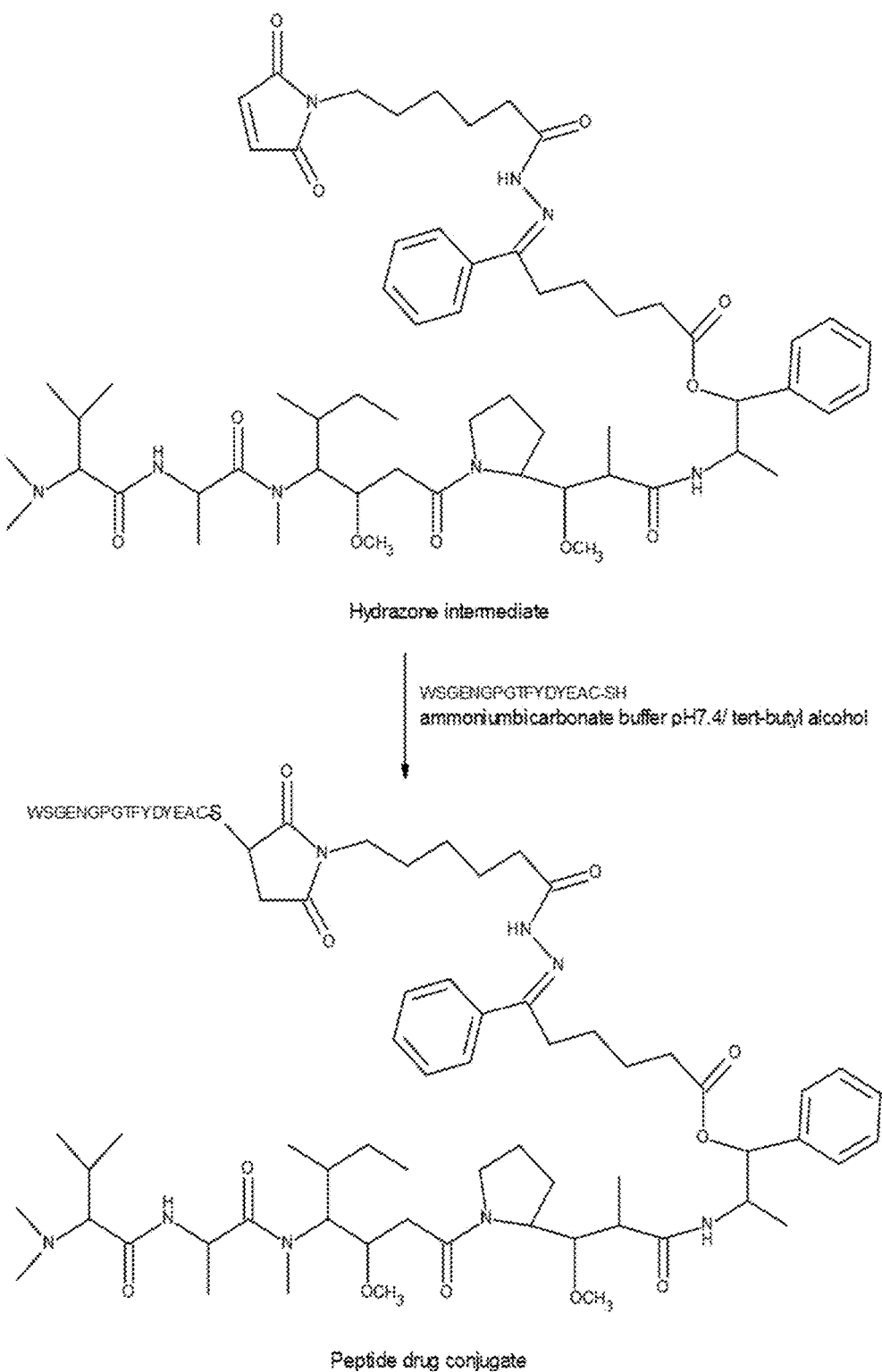
FIG. 17 shows synthesis of a peptide (SEQ ID NO: 83) drug conjugate.

Peptide with a free thiol group (e.g., WSGENGPGTFY-DYEAC-SH, SEQ ID NO: 83) and the hydrazone intermediate were dissolved separately in tert-butyl alcohol and 50 mM ammonium bicarbonate buffer pH 7.4 (1:3). The pH of both solutions was adjusted to 7.4. Peptide was added to the hydrazone solution dropwise, and the reaction mixture was stirred for 10 minutes. The reaction mixture was then directly purified through HPLC using a gradient of triethyl ammonium acetate (TEAA) buffer pH 7 and acetonitrile. Finally, the resulting product was lyophilized. See FIG. 17.

Peptide-Drug Conjugate pH Hydrolysis Studies

Peptide-drug conjugate was evaluated for half-life determination at pH 5 and 7.4. For this, a 1 mg/mL concentration of PDC was incubated in ammonium bicarbonate buffers, pH 5 and 7.4. Degradation of PDC was evaluated by calculating the area under the curve after 0, 0.5, 1, 2, 4, 6 and 48 hours using HPLC with a gradient method, with TEAA buffer pH 7 and acetonitrile.

See Table 4 for MS and HPLC data for the MMAE, its intermediates, and the PDC.

In Vitro Cytotoxicity of Peptide-Drug Conjugate

Cytotoxicity studies of auristatin E, peptide, peptide-drug conjugate and cetuximab were performed on A431, MDA-MB-468 and HEK 293 cells. Cells were cultured to 80% confluency in T75 culture flasks using Dulbecco's Modified Eagle's Medium (DMEM) as growth medium. The cell density was determined using a Coulter Counter. The cells were seeded onto 96 well plates and grown for 24 h. to 50% confluency. This was followed by treatment with various concentrations of the drug auristatin E (AE), peptide-drug conjugate, peptide, and cetuximab ranging from 0.00001 to 10000 nM for 72 h. at 37° C. At the end of the incubation period, the cells were fixed using 10% trichloroacetic acid, followed by washing with distilled water and drying. The cellular proteins were stained using 50 μL of 0.4% sulforhodamine B (SRB) in 1% acetic acid. Unbound SRB was washed with 1% acetic acid and the plates were dried overnight. The cell-bound SRB was then solubilized using 200 μL of 10 mM unbuffered Tris base solution. SRB absorbance was measured at 560 nm wavelength using a Plate Reader. The percent viability of cells was plotted as a function of log concentration and data was analyzed in GraphPad Prism Version 5.0 software (GraphPad Software, Inc., California, USA) using a nonlinear-regression curve fit (variable slope four parameter equation).

TABLE 4

MMAE, intermediates and PDC MS and HPLC data

| Molecule | MS (g/mol) [M + H]+ Calculated | MS (g/mol) [M + H]+ Observed | HPLC Purity (%) |
|---|---|---|---|
| Monomethyl auristatin E (MMAE) | 718.2 | 720.5 | 99 |
| Auristatin E (AE) | 731.2 | 732.5 | 96 |
| AE-benzoylpentanoicacid (AEBPA) | 920.6 | 922.2 | 93 |
| Hydrazone Intermediate | 1127.7 | 1127.6 | 98 |
| Pep11-MMAE conjugate (PDC) | 2922.9 | 2922.8 | 98 |

Figure 18:
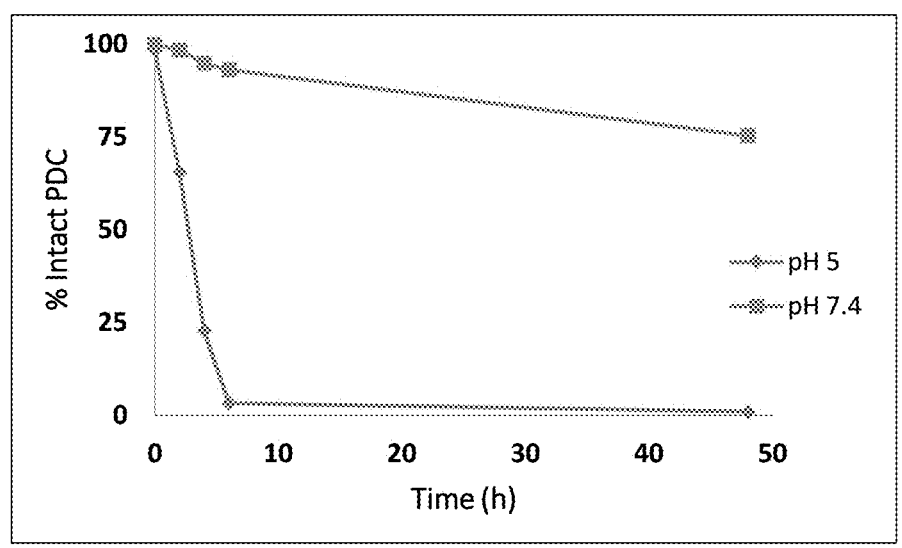
FIG. 18 shows pH hydrolysis studies of PDC at pH 5 and 7.4.

A pH hydrolysis study of the PDC was performed at pH 5 and 7.4. As the PDC has a hydrazone bond, it is important for the PDC to be stable at pH 7.4 and hydrolyze at the acidic pH of 5. Half-life of the PDC was calculated in ammonium bicarbonate buffers, pH 5 and 7.4. The results show that the hydrazone bond was successfully formed and then selectively cleaved at pH 5. The pH can thus be used as a trigger to release the drug from the PDC; for example, when in the low pH environment of cancer cells. The PDC half-life was found to be 2.8 hours at pH 5. PDC was found to be stable at pH 7.4 and its half-life was observed to be more than 48 hours. See FIG. 18 and Table 5.

TABLE 5

Half-life of PDC in pH 5 and 7.4

| pH | Half-life (h) |
|---|---|
| 5 | 2.8 |
| 7.4 | >48 |

Cytotoxicity studies were performed to determine the potency of drug, peptide, peptide-drug conjugate and cetuximab. Percentage of viable cells were calculated using the sulphorhodamine cytotoxicity assay. The drug auristatin E showed similar potency and $IC_{50}$ values across cancer and normal cells, which indicated the non-specificity of the drug. This suggests that a prodrug or a drug-conjugate approach is best suited for use of the drug in treatment.

Figure 19:
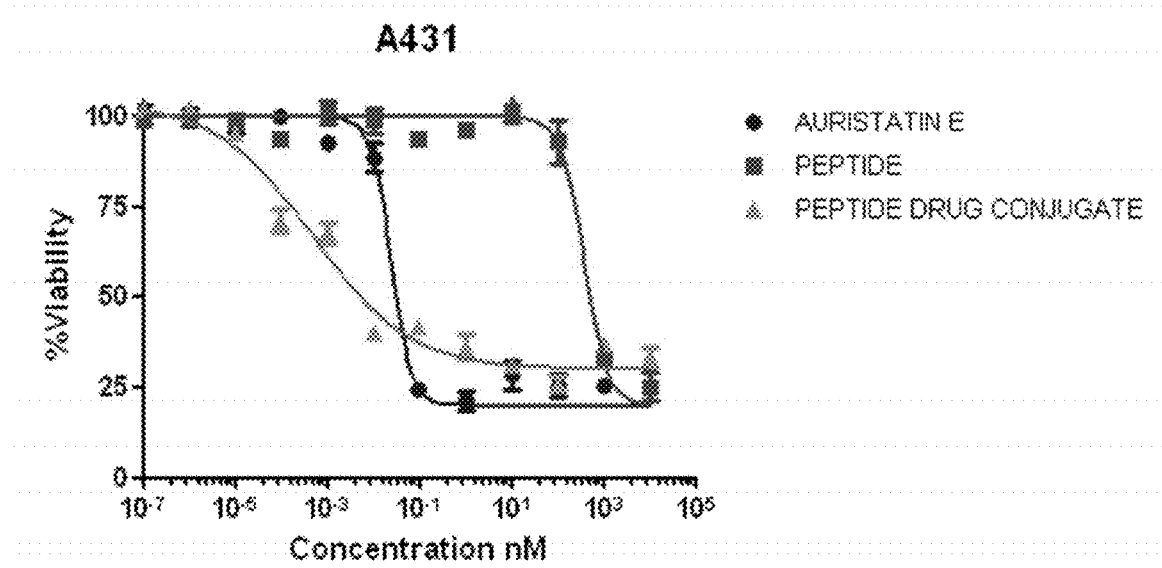
FIG. 19 shows the IC$_{50}$ value of AE, peptide and PDC on A431 cell line.
Figure 20:
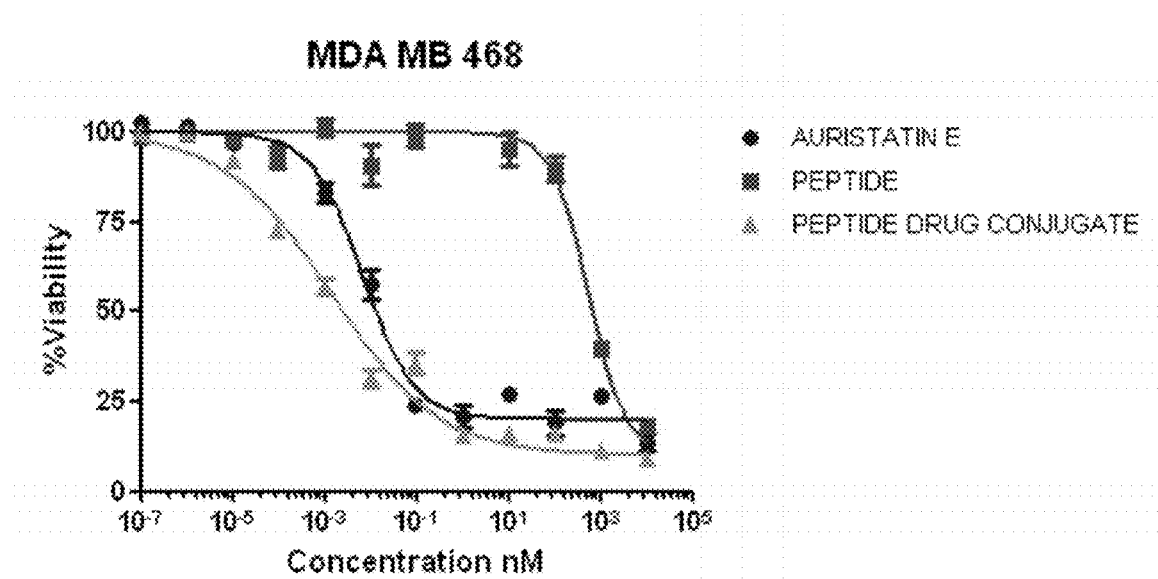
FIG. 20 shows the IC$_{50}$ value of AE, peptide and PDC on cells of the MDA-MB-468 cell line.
Figure 21:
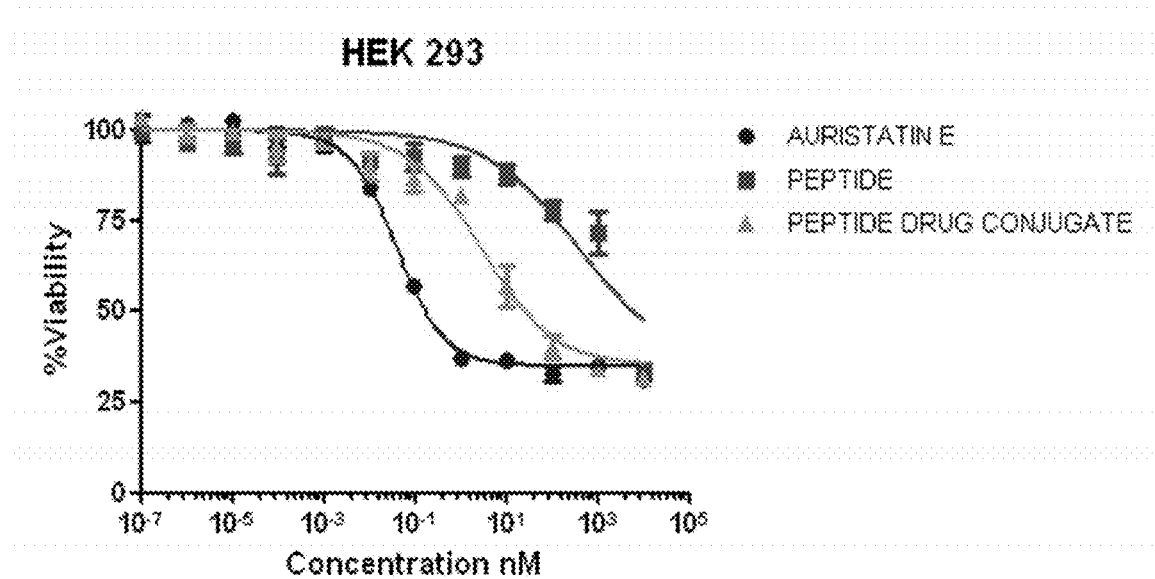
FIG. 21 shows the IC$_{50}$ value of AE, peptide and PDC on HEK 293 cell line.

The peptide itself showed low potency across the cancer cell lines that over-express EGFR (i.e., A431 and MDA-MB-468) as compared with the drug. See FIGS. 19 and 20. The antibody mimic peptide showed selectivity towards cancer cells over normal cells, as it demonstrated 2- to 3-fold lower potency towards control cells (HEK 293) as compared to cancer cells that over-express EGFR. See FIGS. 19-21. Peptide-drug conjugate was found to be around 10-fold more potent as compared to the drug itself towards EGFR over-expressing cancer cells. PDC also showed significantly low potency in HEK 293 cells, which do not overexpress EGFR, relative to cells that overexpress EGFR. This clearly demonstrated that the peptide-drug conjugate selectively bound to, and was internalized via receptor-mediated endocytosis by, cells which over-express EGFR. See FIGS. 19-21 and Table 6.

It is proposed that the cell killing mechanism of PDCs starts upon binding of the targeting peptide to the EGFR, which is overexpressed on the surface of the cancer cells. After binding, the PDC-EGFR complex undergoes internalization through receptor-mediated endocytosis. EGFR is known to be internalized relatively quickly after binding to ligand. Following internalization, the whole PDC-EGFR complex is degraded within the lysosome, which is acidic in pH and rich in proteolytic enzymes. This results in the release of the cytotoxic agent (in our examples, AE), which then exerts its cytotoxic affect by binding to intracellular tubulin and inhibiting its polymerization, which leads to apoptosis of the target cell.

Figure 22:
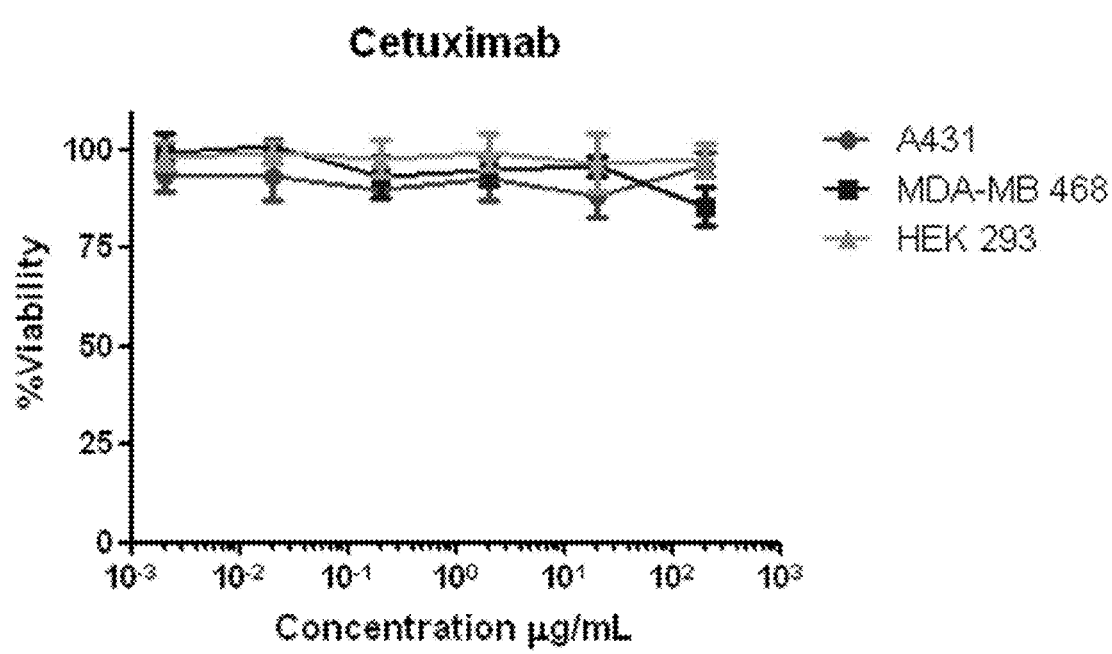
FIG. 22 shows percent viability after cetuximab treatment on different cell lines.

Finally, because cetuximab demonstrated virtually no cytotoxic effects (FIG. 22) (i.e., is virtually harmless to cells), cetuximab conjugated to the peptides described herein present an excellent option for use in PDCs.

TABLE 6

$IC_{50}$ value of AE, peptide, PDC and cetuximab across different cell lines

| | $IC_{50}$ nM | | | |
|---|---|---|---|---|
| Cell Line | Auristatin E | Peptide | Peptide-Drug Conjugate | Cetuximab |
| A431 | 0.0246 | 387.7 | 0.0026 | NA |
| MDA-MB-468 | 0.0117 | 420.3 | 0.0013 | NA |
| HEK 293 | 0.06258 | 1037.0 | 5.807 | NA |

HER2

Peptides were synthesized with motif sequences comprising amino acids corresponding to knob amino acids in pertuzumab which fit sockets on the HER2 epitope in the antibody-epitope binding interface. There were a total of eight knobs on pertuzumab, including T30, D31, Y32, N53, S54, Q61, R73, and G97. See FIG. 23. For peptide sequences, see Table 7.

TABLE 7

| HER2-targeting peptide motif sequences | | | |
|---|---|---|---|
| Name | Sequence | E | Binding site on HER2 |
| Pertuzumab | | | 128 235 245 254 257 268 286 290 295 296 311 |
| HER2-Pep1 | VTYDTGDRAPNSVGSTTKQ (SEQ ID NO: 26) | -35.10 | 249 250 285 303 304 308 310 311 313 314 |
| HER2-Pep2 | VTYDTGNRAPNSVGSLGKQ (SEQ ID NO: 27) | -39.56 | 252 258 259 285 286 290 292 293 294 295 296 297 311 313 325 326 327 329 |
| HER2-Pep3 | VGYDTGLRAPNSVGSTTKQ (SEQ ID NO: 28) | -35.84 | 252 257 258 259 285 286 287 308 311 |
| HER2-Pep4 | VGYDTGLRAPNSVGSLGKQ (SEQ ID NO: 29) | -37.51 | 8 83 84 235 236 245 252 257 258 259 270 285 286 290 291 292 294 |
| HER2-Pep5 | LTYDTGLRAPNSVGSIYKQ (SEQ ID NO: 30) | -41.33 | 12 13 236 245 246 248 249 268 286 288 324 329 330 332 387 389 413 436 |
| HER2-Pep6 | LGYDTGLRAPNSVGSTTKQ (SEQ ID NO: 31) | -34.60 | 81 127 234 235 236 244 245 252 257 258 259 286 288 294 295 296 297 311 |
| HER2-Pep7 | VGYDTGLRAPNSVGSTKQ (SEQ ID NO: 32) | -38.27 | 81 83 127 128 156 235 268 269 289 290 291 292 294 295 296 297 |
| HER2-Pep8 | LTYDTGLRAPNSVGSYKQ (SEQ ID NO: 33) | -34.91 | 236 245 252 254 255 257 268 270 286 287 288 294 295 297 311 |
| HER2-Pep9 | LGYDTGLRAPNSVGSTKQ (SEQ ID NO: 34) | -34.46 | 238 243 245 246 247 248 251 262 286 292 293 294 295 321 326 |
| HER2-Pep10 | QKTTSGVSNPARLGTDYGV (SEQ ID NO: 35) | -41.35 | 59 83 128 154 234 235 236 244 245 269 270 288 289 290 291 295 326 329 |
| HER2-Pep 11 | QYTGSNEPARSLGTDNGP (SEQ ID NO: 36) | -48.67 | 35 59 236 245 268 269 270 281 286 287 289 290 291 292 325 326 327 329 |
| HER2-Pep12 | QNYTFGVPSEARLGTDVTL (SEQ ID NO: 37) | -35.97 | 466 467 465 279 306 304 276 266 275 274 239 273 249 272 237 263 264 |
| HER2-Pep13 | QKTSGVSNPARLCITDYGV (SEQ ID NO: 38) | -37.66 | 5 6 8 417 414 413 324 325 329 326 291 292 290 234 83 235 128 154 244 216 |
| HER2-Pep14 | QKTSGVSNPARLGTEYGV (SEQ ID NO: 39) | -34.09 | 258 312 298 311 285 268 286 259 287 251 248 266 250 252 |
| HER2-Pep15 | QKGLSGVSNPARNGTDYTV (SEQ ID NO: 40) | -34.15 | 296 255 252 256 257 258 259 250 311 286 285 262 308 |
| HER2-Pep16 | QKGLSGVSNPARNGTEYT (SEQ ID NO: 41) | -34.09 | 252 286 311 248 238 247 243 250 285 249 246 245 227 244 |
| HER2-Pep17 | QKYISGVSNPARLGTDYTL (SEQ ID NO: 42) | -36.56 | 264 246 247 248 243 251 226 227 239 216 251 252 253 254 255 |
| HER2-Pep18 | LTKDTGLRAPNSVSYIFGQ (SEQ ID NO: 43) | -40.62 | 245 248 249 250 252 257 258 259 268 285 286 287 296 311 313 |
| HER2-Pep19 | QNYISGVSPKARLGTDYTL (SEQ ID NO: 44) | -37.10 | 330 329 327 326 296 295 297 252 311 285 308 303 |
| HER2-Pep20 | QNYIFSGVSKARLGTDYTV (SEQ ID NO: 45) | -33.74 | 315 314 312 313 298 300 301 281 466 278 279 305 430 437 438 465 281 5 4 3 1 |
| HER2-Pep21 | PGNDTGLSRAPENSGFTYQ (SEQ ID NO: 46) | -45.72 | 295 316 317 293 349 297 299 300 201 307 321 319 298 327 326 341 437 304 305 279 410 347 383 310 |
| HER2-Pep22 | TSPQGYPNDAGFLGRESTN (SEQ ID NO: 47) | -29.66 | 2 57 231 233 237 278 301 304 306 410 438 |

As shown in Table 7, peptide motif sequences HER2-Pep1 to HER2-Pep10 had a pattern of *YDT*R*PNS*G*Q* (SEQ ID NO: 84), where Y, D, T, R, N, S, G, Q correspond to knob-forming amino acids in pertuzumab which pack sockets in the HER2 epitope. The P residue was introduced in the sequences as a tertiary structure constraint. The (*) here represents no amino acid and/or one or more amino acids that can be used as spacers.

Peptide motif sequences HER2-Pep11 to HER2-Pep21 had a pattern of QYTFG<u>S</u>NEPA<u>R</u>SLG<u>T</u><u>D</u>NGP (SEQ ID NO: 36), where Q, S, N, R, T and D (underlined) correspond to knob-forming amino acids in pertuzumab, which pack sockets in the HER2 epitope. The P residue at the ninth position in these sequences was introduced as a tertiary structure constraint. The residues not underlined are amino acids which fill the spaces between the knobs.

FIG. 23 shows a 2-dimensional schematic of the packing interface between pertuzumab and HER2. It is a simplified lattice diagram represented by the Knob-Socket model. There are a total of 20 sockets formed by the HER2 epitope at the binding interface. Sockets that are packed by the same knob are represented in the same gray scale (see, e.g., the knob labeled D31). Residues forming sockets are presented along the solid black line, and residues not involved with packing are omitted or shown as small gray dot.

Twenty-two peptides were designed, including one control HER2-PEP22, which has the scrambled sequence of HER2-PEP11. See Table 7. The estimated docking energy for all (non-scrambled) peptides ranged from −33.7 kcal/mol to −48.7 kcal/mol. By comparison, the scrambled peptide had an estimated docking energy of −29.7 kcal/mol. Peptides HER2-PEP7, HER2-PEP11, HER2-PEP16, HER2-PEP20, HER2-PEP21 and HER2-PEP22 were synthesized and further evaluated.

All HER2-PEPs were designed and synthesized by solid phase peptide synthesis to be used for binding studies with HER2 protein by Surface Plasmon Resonance (SPR). FITC labeled HER2-PEPs were also synthesized for cellular binding and uptake studies by confocal microscopy and flow cytometry.

In Vitro Binding Specificity

HER2 protein was known to be overexpressed on various cancer cells. Since HER2 is located on cellular surface, the major methodology for the determination of binding with HER2 is using imaging studies. The binding of peptides to HER2-overexpressed cells can be studied using fluorescence based imaging techniques. The FITC tag helps visualize and localize the peptides after being incubated with cells, when observed using high-resolution electron microscopy such as confocal laser scanning microscopy. The advantage of confocal microscopy is its point illumination, which eliminates out-of-focus light rays, producing images with better resolution and reduced background signal. Additionally, a confocal laser scanning microscope slices a thick sample into thin sections and scans the image at different focal planes or depths within the sample. This helps in building a three dimensional image of the sample.

In addition to confocal microscopy, which permits a qualitative study of the binding between antibody mimics and cells, flow cytometry can be used to quantify the fluorescence of cell samples. Flow cytometry is a technology that analyzes the physical and chemical characteristics of particles in a fluid when the particles pass through flow chamber.

The binding specificity of peptides toward HER2 was evaluated by incubating the peptides in solution with different cell lines. MDA-MB-361 and ZR-75-1 are breast cancer cells that are known to express HER2 at high and medium levels. These two HER2 positive cell lines and one HER2 negative cell line, HEK293 (human embryonic kidney cell), were used for binding specificity studies. By using confocal microscopy, peptides were visualized and located with a FITC tag after incubation, to determine whether they bound specifically to HER2 positive cells. With flow cytometry, the fluorescence of cell samples after incubation with different antibody mimics could be precisely determined and used to analyze the extent of binding of the peptides.

HER2 positive cells MDA-MB-361 and ZR-75-1, and control cell HEK293, were purchased from ATCC (Manassas, Va., USA). Cell culture reagents including Dulbecco's modified eagle's medium (DMEM), L-Glutamine, Trypsin (TrypLE Express), Hanks Balanced Salt Solution (HBSS), Recovery cell culture freezing media, Alexa fluor 594 wheat germ agglutinin and Slow fade gold mounting medium were purchased from Invitrogen (Carlsbad, Calif., USA). Penicillin-Streptomycin was obtained from Cellgro, Mediatech Inc. (VA, USA). Hyclone Fetal Bovine Serum (FBS) was purchased from Thermo Scientific (Logan, Utah, USA). All microscopy supplies were purchased from VWR (USA). FACS Calibur™ flow cytometer and BD CellQuest™ Pro software were purchased from BD biosciences (USA). Cell culture supplies were purchased from Santa Cruz Biotechnology Inc. (TX, USA).

Cell culture media was prepared by adding 10% FBS, 1% penicillin streptomycin (5000 I.U./mL) and 1% L-Glutamine (200 mM) to the DMEM. The media was stored in a refrigerator until use. MDA-MB-361 and ZR-75-1 cells were cultured and maintained in T75 flasks (growth area, 75 $cm^2$) in the prepared DMEM at 37° C. and 5% $CO_2$, and were passed when the confluency reached about 80%. The cells were frozen in recovery freezing media and kept in nitrogen cans for future use.

Confocal Microscopy Studies

MDA-MB-361, ZR-75-1 and HER293 cells were grown in T75 flasks at 37° C. and 5% $CO_2$. Upon reaching 80% confluency, the cells were counted and seeded onto coverslips placed inside 6-well culture plates at a density of 80,000 cells/well. The cells were allowed to attach for 24 hours before the experiment was performed. Upon attachment, the cells were washed twice with HBSS and serum free media.

Stock solutions of FITC labeled HER2-PEPs and control peptide were prepared with dimethyl sulfoxide (DMSO). Stock solutions were diluted with serum free media medium several times and less than 1% of DMSO was presented in the final solutions of all peptides (10 μM), which were added to the 6-well culture plates.

After incubating 15 minutes at 37° C., the medium was removed and the cells were washed twice with HBSS. The cells were then treated with a 2.5 μg/mL solution of Alexa fluor 594 wheat germ agglutinin in HBSS for 10 minutes to stain the cell plasma membrane. The dye solution was removed and cells were washed twice with HBSS. The cells were then fixed by performing a 15 minute treatment using 4% paraformaldehyde solution prepared in HBSS. The cells were washed with HBSS followed by a final wash of distilled water. A 10 μL drop of the mounting medium (slow fade gold) was placed on the microscopic slides and the coverslips with the fixed cells were placed on the slides. The coverslips were then sealed on all four sides. The slides were imaged on a Leica DMIRE2 confocal laser scanning microscope with Yokogawa spinning disk using 64× magnification and oil immersion. The FITC fluorescence was visualized using 491 nm and the Alexa fluor 594 fluorescence was visualized using 561 nm wavelength filter.

Flow Cytometry Studies

Flow cytometric studies were carried out to quantify the fluorescence intensity of cells after being incubated with FITC labeled mimics. MDA-MB-361, ZR-75-1 and HEK293 cells were seeded in 6-well culture plates at a density of $3\times10^5$ cells per well for 24 hours and then incubated with FITC labeled mimics at a concentration of 10 µM in HBSS at 37° C. for 15 minutes. After washing with HBSS twice, cells remaining on the plates were trypsinized with Trpsin-EDTA and centrifuged at 1500 rpm for 5 min. Supernatant was removed and cell pellets were resuspended in 1 ml of HBSS. The suspension was transferred to a FACS Calibur™ flow cytometer and cell fluorescence was measured with high dynamic range photomultipliers with a 530 nm filter. Quantitative changes of fluorescence in different cells samples were assessed by mean fluorescence intensity (MFI), and FACS data were analyzed using BD CellQuest™ Pro software. Paired t-tests were used to determine statistical significance using the GraphPad Prism 5® Software. P-values less than or equal to 0.05 were considered to be statistically significant.

Results

Confocal microscopy was used to study the in vitro binding specificity of antibody mimics to HER2 positive cancer cells. Cell images (not shown) taken by confocal microscopy showed that FITC labeled antibody mimics can bind to MDA-MB-361 and ZR-75-1 cells but not HEK293 cells. After incubation with 10 µM of FITC labeled antibody mimics solution, significant fluorescence were observed on cellular surfaces of MDA-MB-361 and ZR-75-1 cells while no fluorescence was detected on HEK293 cells. In contrast, the FITC labeled control peptide HER2-PEP22 showed no binding to all the three cell lines. The significant fluorescence of MDA-MB-361 and ZR-75-1 cells could be a result from specific interaction between HER2 and antibody mimics, which was further confirmed by SPR binding affinity results in the next section.

In the confocal microscopy studies, Alexa Flour 594 dye was used to colorize cell plasma membrane to help us visualize the cell. Results demonstrated that, except for binding on the cell surface, antibody mimics showed partially internalization by cells to different extents. A possible mechanism of internalization of antibody mimics is receptor-mediated endocytosis upon binding onto HER2 protein. Differing from antibodies, antibody mimics are less than 1/50th of the mass of their corresponding antibodies, which makes it much easier for their internalization by cells. This characteristic of peptides may be further used for targeting delivery of drugs into HER2 overexpressed cancer cells.

Results from the confocal microscopy studies suggested that the newly designed antibody mimics could bind to HER2 positive cell lines. For further quantitative analysis of the binding ability of these antibody mimics towards HER2 overexpressed cell lines, flow cytometry studies were carried out to quantify the fluorescence of HER2 positive and negative cells before and after incubation with different cells. FACS histograms were obtained for different samples. Based on these histograms, significant fluorescence peak shift were observed for HER2 positive cells incubated with antibody mimics except control peptide HER2-PEP22. In contrast, HER2 negative cells only showed little increase of the fluorescence, which may result from non-specific binding, and absorption of all the antibody mimics.

Mean fluorescence intensity (MFI) for all samples were analyzed based on histograms using BD CellQuest™ Pro software. The MFI of MDA-MB-361, ZR-75-1, and HEK 293 cells in blank HBSS were 4.5±0.2, 3.2±0.4 and 3.1±1.0, respectively, and the corresponding MFI after incubation with control peptide FITC-HER2-PEP22 were 22.1±0.5, 19.6±3.2 and 14.7±1.7, respectively. In contrast, when incubated with FITC labeled antibody mimics, the MFI of MDA-MB-361 and ZR-75-1 cells were 3- to 21-fold higher than that of FITC labeled control peptide HER2-PEP22 (P<0.001). Additionally, the MFI for MDA-MB-361 and ZR-75-1 cells incubated with antibody mimics were 4- to 60-fold higher than HEK 293 cells after same incubation treatment (P<0.001). No significant difference in MFI was observed between HEK293 cells treated with FITC labeled antibody mimics and control peptide. These results suggested that newly designed antibody mimics can bind specifically to HER2 positive cells, which was consistent with results from confocal microscopy studies.

Binding Affinity Studies Using SPR

Dual Channel SPR Spectrometer SPR7000DC and SR7000 Gold Sensor chip (500,000 Da Carboxymethyl Dextran) were purchased from Reichert Technologies (USA). HER2 recombinant human protein was purchased from Life Technologies™ Thermo Fisher Scientific Inc. Pertuzumab was a gift from Stockton Hematology Oncology Medical Group. Scrubber 2® software was download from BioLogic Software. N-ethyl-N'-(3-dimethylaminopropyl) carbodiimide (EDC), N-hydroxysuccinimide (NHS), Ethanolamine (EA), and glycine were purchased from Thermo Scientific Inc. Bovine serum albumin (BSA) was purchased from Sigma-Aldrich.

To confirm that antibody mimics have the anticipated binding affinity towards HER2 protein, SPR studies were performed using the Dual Channel SPR Spectrometer SPR7000DC. All experiments were carried out at 25° C. with a data collection rate of 2 Hz. The running method was created using the Autolink control software. PBS with 0.01% Tween 20 (pH7.4) buffers were filtered and thoroughly degassed before use. HER2 recombinant human protein was covalently attached to the left channel of a 500,000 Da carboxymethylated dextran sensor chip using EDC and NHS chemistries. Then, the chip was blocked by passing EA for 8 minutes at a rate of 10 µL/min. All antibody mimics and Pertuzumab were injected as soluble analytes in PBS with 0.01% Tween 20 at different concentrations with an injection speed of 15 µL/min. Triplicate determinations were done at each concentration. The bound surface was regenerated by sequential injections of 10 mM glycine in PBST (pH 2.5).

The sensorgrams from SPR were globally treated using Scrubber 2® software where all traces were zeroed, cropped, aligned, and referenced. Kinetic constants ka and kd were determined by global fitting analyses of the titration curves using the 1:1 Lagmurian interaction model taking into account the mass transport. The equilibrium dissociation constant (KD) was calculated from the kd/ka ratio.

To test the binding specificity of antibody mimics to HER2 protein, all peptides were injected through a carboxymethylated dextran sensor chip that was immobilized with bovine serum albumin (BSA). In addition to testing the control peptide HER2-PEP22 on HER2 immobilized sensor chip, we also tested two peptides EGFR-PEP11 and EGFR-PEP22 designed for binding with EGFR in the SPR studies.

Additionally, specific peptides were used for competition studies with Pertuzumab in SPR. For competition studies, two methods were used: sequential injections of antibody mimic and Pertuzumab, and co-injection of antibody mimic and Pertuzumab (i.e., in a mixture).

In the sequential injection studies, Pertuzumab solution was first injected onto the surface chip immobilized with HER2, followed by regeneration of the surface using 10 mM glycine solution (pH=2.5). Then, antibody mimic solution was injected, followed by injection of Pertuzumab solution without regeneration to see the competitive effect of antibody mimic remaining on the surface chip for binding between HER2 and Pertuzuma In another experiment, antibody mimic solution was first injected onto the sensor chip, followed by regeneration of the surface using 10 mM glycine solution (pH=2.5). Then, Pertuzumab solution was injected onto the sensor chip followed by injection of antibody mimic solution without regeneration to see the competitive effect of any Pertuzumab remaining on the surface chip for binding between HER2 and the antibody mimic.

In the co-injection studies, solutions with different ratios of Pertuzumab and antibody mimic mixture were injected onto sensor chip to study competition between Pertuzumab and antibody mimic for binding with HER2. The apparent response (RU) results from both Pertuzumab and HER2-PEP11 binding to HER2 on the sensor chip. The sensorgrams with different apparent responses (RU) were then used to calculate the contribution of Pertuzumab and HER2-PEP11 based on the response (RU) from individual sensorgrams of pure Pertuzumab and HER2-PEP11 respectively. The percentage of replacement (X) of Pertuzumab by HER2-PEP11 can be calculated by using following equations:

$$R_{apparent} = R_{pertuzumab} \times (1-X) + R_{HER2\text{-}Pep11} \times X,$$

$$X = ((R_{apparent} - R_{pertuzumab})/(R_{HER2\text{-}Pep11} - R_{pertuzumab})) \times 100\%,$$

where $R_{apparent}$ is apparent response based on sensorgram from co-injection studies, $R_{pertuzumab}$ is response based on sensorgram from individual injection of Pertuzumab with same concentration used in co-injection studies, and $R_{HER2\text{-}Pep11}$ is response based on sensorgram from individual injection of HER2-PEP11 with same concentration used in co-injection studies.

Sensorgrams were obtained from binding studies of different antibody mimics and Pertuzumab with HER2. For kinetics analysis, different concentrations of antibody mimics and Pertuzumab were passed over sensor chip with HER2 in order of increasing slop from lowest concentration to the highest concentration. For the sensorgram of antibody mimics, the curves exhibited fast on and off rates and reach equilibrium state rapidly which is very common in the studies of peptides molecules. Both kinetic constants ka and kd were determined by global fitting analyses of the titration curves using the 1:1 Lagmurian interaction model in software Scrubber. Results showed that the control peptide HER2-PEP22 had the lowest ka (130.9 $M^{-1}s^{-1}$) and highest kd (0.0181 $s^{-1}$), resulting in a calculated $K_D$ of 138.297 μM which is about 2000 fold higher than that of antibody mimics HER2-PEP11 ($K_D$=55.4 nM) and HER2-PEP21 ($K_D$=56.0 nM). Since HER2-PEP22 is scrambled sequence of HER2-PEP11, the SPR results proved the importance of design the proper amino acids as knobs to fit into different sockets on HER2 for preserve binding specificity and affinity. HER2-PEPDE and HER2-PEPDF, with sequences based on the CDR sequences of pertuzumab, have $K_D$ of 323 nM and 410 nM respectively, which are much higher than that of HER2-PEP7 ($K_D$=93.0 nM), HER2-PEP11 ($K_D$=55.4 nM), HER2-PEP16 ($K_D$=247.0 nM) and HER2-PEP21 ($K_D$=56.0 nM). This demonstrates the peptides disclosed herein have improved binding of HER2. By comparison the antibody pertuzumab has a $K_D$ of 54.9 pM as measured by SPR. PD1 and PDL1

By using the same method for generation EGFR and HER2, additional peptides for PD1 and PDL1 were generated as listed in Tables 8-10 below.

TABLE 8

PD 1: Short peptides

| | |
|---|---|
| SEQ ID NO: 48 | LSYEFLLF |
| SEQ ID NO: 49 | LKFLLFAF |
| SEQ ID NO: 50 | LSIEFLPV |
| SEQ ID NO: 51 | LSEEFLIL |
| SEQ ID NO 52 | HLFEILMF |
| SEQ ID NO: 53 | HSEFFLTL |
| SEQ ID NO: 54 | LKEYFFLL |
| SEQ ID NO: 55 | LKEFYFLL |
| SEQ ID NO: 56 | SKYFPMAF |
| SEQ ID NO: 57 | LKEYFLPL |

TABLE 9

PD1: Longer peptides

| | |
|---|---|
| SEQ ID NO: 58 | GLKEPVGYLGFGLPLGLF |
| SEQ ID NO: 59 | GLKEIPDYLGFGLPLGLF |
| SEQ ID NO: 60 | GLKEIPDYAGFGIPLGVD |
| SEQ ID NO: 61 | GLSIPVGYLGFGIPLGLP |
| SEQ ID NO: 62 | QLSIPVGYAGFGLPLGAP |
| SEQ ID NO: 63 | QLKEIPDYVSFAPLGADF |
| SEQ ID NO: 64 | GLKEPVGYLGFGLPGADF |
| SEQ ID NO: 65 | NHSE1PDFLGYGLPGADF |
| SEQ ID NO: 66 | QLSIEPVFLGYGLPLGLD |
| SEQ ID NO: 67 | ALKISEPVYLGFAPLVGD |

TABLE 10

PD-L1

| | |
|---|---|
| SEQ ID NO: 68 | IAPDYSQERDTIEGKTPVR |
| SEQ ID NO: 69 | IAPDYSQELDPIEGKTPVR |
| SEQ ID NO: 70 | IAPDYSQERDTIAGKTPVR |
| SEQ ID NO: 71 | IAPDYSQELDPIAGKTPVR |
| SEQ ID NO: 72 | IAPDYSQELDPIAGKTPVR |
| SEQ ID NO: 73 | IASDYSQERDTIEGKTPVR |
| SEQ ID NO: 74 | ILPDYSQELDPIEGKTPVR |
| SEQ ID NO: 75 | VAPDYSQERDTIAGKTPVR |
| SEQ ID NO: 76 | LAPDYKQELDPIAFKTPVR |
| SEQ ID NO: 77 | IAPDYSQELDPIVNVTPVR |

What is claimed is:

1. An isolated antibody mimic peptide comprising a sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, and 24.

2. A pharmaceutical composition of claim 1, wherein the composition comprises the antibody mimic peptide of claim 1 and a pharmaceutically acceptable carrier.

3. An isolated antibody mimic peptide consists of SEQ ID NO: 1, 2, 3, 4, 5, 6, 7, 8, 9, 10, 11, 12, 13, 14, 15, 16, 17, 18, 19, 20, 21, 22, 23, or 24.

4. A pharmaceutical composition of claim 3, wherein the composition comprises the antibody mimic peptide of claim 3 and a pharmaceutically acceptable carrier.

5. The antibody mimic peptide of claim 1, wherein the peptide binds to EGFR.

6. The peptide of claim 1, herein the peptide is conjugated to a substance.

7. The peptide of claim 3, wherein the peptide is conjugated to a substance.

* * * * *

SEQUENCE LISTING

<160> NUMBER OF SEQ ID NOS: 84

<210> SEQ ID NO 1
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 1

Trp Ser Gly Glu Asn Gly Pro Gly Tyr Tyr Asp Tyr Glu Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 2

Trp Ser Gly Glu Asn Gly Pro Gly Tyr Trp Asp Tyr Glu Ala
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 3

Trp Ser Gly Glu Asn Gly Pro Gly Tyr Leu Asp Tyr Glu Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 4

Trp Ser Gly Glu Asn Gly Pro Gly Tyr Ile Asp Tyr Glu Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 5

Trp Ser Gly Glu Asn Gly Pro Gly Tyr Val Asp Tyr Glu Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 6

Trp Ser Gly Glu Asn Gly Pro Gly Tyr Phe Asp Tyr Glu Ala
1               5                   10

```
<210> SEQ ID NO 7
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 7

Trp Ser Gly Glu Asn Gly Pro Gly Trp Tyr Asp Tyr Glu Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 8

Trp Ser Gly Glu Asn Gly Pro Gly Leu Tyr Asp Tyr Glu Ala
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 9

Trp Ser Gly Glu Asn Gly Pro Gly Ile Tyr Asp Tyr Glu Ala
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 10

Trp Ser Gly Glu Asn Gly Pro Gly Val Tyr Asp Tyr Glu Ala
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 11

Trp Ser Gly Glu Asn Gly Pro Gly Phe Tyr Asp Tyr Glu Ala
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 12

Trp Ser Gly Glu Asn Gly Pro Gly Thr Tyr Tyr Asp Tyr Glu Ala
1               5                   10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 13

Trp Ser Gly Glu Asn Gly Pro Gly Thr Tyr Trp Asp Tyr Glu Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 14

Trp Ser Gly Glu Asn Gly Pro Gly Thr Tyr Leu Asp Tyr Glu Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 15

Trp Ser Gly Glu Asn Gly Pro Gly Thr Tyr Ile Asp Tyr Glu Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 16

Trp Ser Gly Glu Asn Gly Pro Gly Thr Tyr Val Asp Tyr Glu Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 17

Trp Ser Gly Glu Asn Gly Pro Gly Thr Tyr Phe Asp Tyr Glu Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 18

Trp Ser Gly Glu Asn Gly Pro Gly Thr Trp Tyr Asp Tyr Glu Ala
1               5                   10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 19

Trp Ser Gly Glu Asn Gly Pro Gly Thr Leu Tyr Asp Tyr Glu Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 20

Trp Ser Gly Glu Asn Gly Pro Gly Thr Ile Tyr Asp Tyr Glu Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 21

Trp Ser Gly Glu Asn Gly Pro Gly Thr Val Tyr Asp Tyr Glu Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic amino acid - EGFR

<400> SEQUENCE: 22

Trp Ser Gly Glu Asn Gly Pro Gly Thr Phe Tyr Asp Tyr Glu Ala
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 23

Ala Glu Tyr Asp Tyr Phe Gly Pro Gly Asn Glu Gly Ser Trp
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic amino acid - EGFR

<400> SEQUENCE: 24

Ala Glu Tyr Asp Phe Tyr Gly Pro Gly Asn Glu Gly Ser Trp
1               5                   10

<210> SEQ ID NO 25
```

-continued

```
<211> LENGTH: 14
<212> TYPE: PRT
<213> ORGANISM: Artificial Sequence
<220> FEATURE:
<223> OTHER INFORMATION: Synthetic amino acid - Control

<400> SEQUENCE: 25

Ser Gly Glu Trp Ala Tyr Asp Gly Tyr Glu Pro Asn Phe Gly
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 26

Val Thr Tyr Asp Thr Gly Asp Arg Ala Pro Asn Ser Val Gly Ser Thr
1               5                   10                  15

Thr Lys Gln

<210> SEQ ID NO 27
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 27

Val Thr Tyr Asp Thr Gly Asn Arg Ala Pro Asn Ser Val Gly Ser Leu
1               5                   10                  15

Gly Lys Gln

<210> SEQ ID NO 28
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 28

Val Gly Tyr Asp Thr Gly Leu Arg Ala Pro Asn Ser Val Gly Ser Thr
1               5                   10                  15

Thr Lys Gln

<210> SEQ ID NO 29
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 29

Val Gly Tyr Asp Thr Gly Leu Arg Ala Pro Asn Ser Val Gly Ser Leu
1               5                   10                  15

Gly Lys Gln

<210> SEQ ID NO 30
<211> LENGTH: 19
<212> TYPE: PRT
<213> ORGANISM: Artificial Sequence
<220> FEATURE:
<223> OTHER INFORMATION: Synthetic amino acid - HER 2
```

```
<400> SEQUENCE: 30

Leu Thr Tyr Asp Thr Gly Leu Arg Ala Pro Asn Ser Val Gly Ser Ile
1               5                   10                  15

Tyr Lys Gln

<210> SEQ ID NO 31
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 31

Leu Gly Tyr Asp Thr Gly Leu Arg Ala Pro Asn Ser Val Gly Ser Thr
1               5                   10                  15

Thr Lys Gln

<210> SEQ ID NO 32
<211> LENGTH: 18
<212> TYPE: PRT
<213> ORGANISM: Artificial Sequence
<220> FEATURE:
<223> OTHER INFORMATION: Synthetic amino acid - HER 2

<400> SEQUENCE: 32

Val Gly Tyr Asp Thr Gly Leu Arg Ala Pro Asn Ser Val Gly Ser Thr
1               5                   10                  15

Lys Gln

<210> SEQ ID NO 33
<211> LENGTH: 18
<212> TYPE: PRT
<213> ORGANISM: Artificial Sequence
<220> FEATURE:
<223> OTHER INFORMATION: Synthetic amino acid - HER 2

<400> SEQUENCE: 33

Leu Thr Tyr Asp Thr Gly Leu Arg Ala Pro Asn Ser Val Gly Ser Tyr
1               5                   10                  15

Lys Gln

<210> SEQ ID NO 34
<211> LENGTH: 18
<212> TYPE: PRT
<213> ORGANISM: Artificial Sequence
<220> FEATURE:
<223> OTHER INFORMATION: Synthetic amino acid - HER 2

<400> SEQUENCE: 34

Leu Gly Tyr Asp Thr Gly Leu Arg Ala Pro Asn Ser Val Gly Ser Thr
1               5                   10                  15

Lys Gln

<210> SEQ ID NO 35
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 35

Gln Lys Thr Thr Ser Gly Val Ser Asn Pro Ala Arg Leu Gly Thr Asp
1               5                   10                  15
```

Tyr Gly Val

<210> SEQ ID NO 36
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 36

Gln Tyr Thr Phe Gly Ser Asn Glu Pro Ala Arg Ser Leu Gly Thr Asp
1               5                   10                  15

Asn Gly Pro

<210> SEQ ID NO 37
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 37

Gln Asn Tyr Thr Phe Gly Val Pro Ser Glu Ala Arg Leu Gly Thr Asp
1               5                   10                  15

Val Thr Leu

<210> SEQ ID NO 38
<211> LENGTH: 18
<212> TYPE: PRT
<213> ORGANISM: Artificial Sequence
<220> FEATURE:
<223> OTHER INFORMATION: Synthetic amino acid - HER 2

<400> SEQUENCE: 38

Gln Lys Thr Ser Gly Val Ser Asn Pro Ala Arg Leu Gly Thr Asp Tyr
1               5                   10                  15

Gly Val

<210> SEQ ID NO 39
<211> LENGTH: 18
<212> TYPE: PRT
<213> ORGANISM: Artificial Sequence
<220> FEATURE:
<223> OTHER INFORMATION: Synthetic amino acid - HER 2

<400> SEQUENCE: 39

Gln Lys Thr Ser Gly Val Ser Asn Pro Ala Arg Leu Gly Thr Glu Tyr
1               5                   10                  15

Gly Val

<210> SEQ ID NO 40
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 40

Gln Lys Gly Leu Ser Gly Val Ser Asn Pro Ala Arg Asn Gly Thr Asp
1               5                   10                  15

Tyr Thr Val

```
<210> SEQ ID NO 41
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 41

Gln Lys Gly Leu Ser Gly Val Ser Asn Pro Ala Arg Asn Gly Thr Glu
1               5                   10                  15

Tyr Thr Val

<210> SEQ ID NO 42
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 42

Gln Lys Tyr Ile Ser Gly Val Ser Asn Pro Ala Arg Leu Gly Thr Asp
1               5                   10                  15

Tyr Thr Leu

<210> SEQ ID NO 43
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 43

Leu Thr Lys Asp Thr Gly Leu Arg Ala Pro Asn Ser Val Ser Tyr Ile
1               5                   10                  15

Phe Gly Gln

<210> SEQ ID NO 44
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 44

Gln Asn Tyr Ile Ser Gly Val Ser Pro Lys Ala Arg Leu Gly Thr Asp
1               5                   10                  15

Tyr Thr Leu

<210> SEQ ID NO 45
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 45

Gln Asn Tyr Ile Phe Ser Gly Val Ser Lys Ala Arg Leu Gly Thr Asp
1               5                   10                  15

Tyr Thr Val

<210> SEQ ID NO 46
<211> LENGTH: 19
<212> TYPE: PRT
<213> ORGANISM: Artificial Sequence
```

```
<220> FEATURE:
<223> OTHER INFORMATION: Synthetic amino acid - HER 2

<400> SEQUENCE: 46

Pro Gly Asn Asp Thr Gly Leu Ser Arg Ala Pro Glu Asn Ser Gly Phe
1               5                   10                  15

Thr Tyr Gln

<210> SEQ ID NO 47
<211> LENGTH: 19
<212> TYPE: PRT
<213> ORGANISM: Artificial Sequence
<220> FEATURE:
<223> OTHER INFORMATION: Synthetic amino acid - HER 2

<400> SEQUENCE: 47

Thr Ser Pro Gln Gly Tyr Pro Asn Asp Ala Gly Phe Leu Gly Arg Glu
1               5                   10                  15

Ser Thr Asn

<210> SEQ ID NO 48
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 48

Leu Ser Tyr Glu Phe Leu Leu Phe
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 49

Leu Lys Phe Leu Leu Phe Ala Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 50

Leu Ser Ile Glu Phe Leu Pro Val
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 51

Leu Ser Glu Glu Phe Leu Ile Leu
1               5

<210> SEQ ID NO 52
```

```
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 52

His Leu Phe Glu Ile Leu Met Phe
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 53

His Ser Glu Phe Phe Leu Thr Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 54

Leu Lys Glu Tyr Phe Phe Leu Leu
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 55

Leu Lys Glu Phe Tyr Phe Leu Leu
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 56

Ser Lys Tyr Phe Pro Met Ala Phe
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic amino acid - PD1

<400> SEQUENCE: 57

Leu Lys Glu Tyr Phe Leu Pro Leu
1               5

<210> SEQ ID NO 58
<211> LENGTH: 18
```

```
<212> TYPE: PRT
<213> ORGANISM: Artificial Sequence
<220> FEATURE:
<223> OTHER INFORMATION: Synthetic amino acid - PD1

<400> SEQUENCE: 58

Gly Leu Lys Glu Pro Val Gly Tyr Leu Gly Phe Gly Leu Pro Leu Gly
1               5                   10                  15
Leu Phe

<210> SEQ ID NO 59
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 59

Gly Leu Lys Glu Ile Pro Asp Tyr Leu Gly Phe Gly Leu Pro Leu Gly
1               5                   10                  15
Leu Phe

<210> SEQ ID NO 60
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 60

Gly Leu Lys Glu Ile Pro Asp Tyr Ala Gly Phe Gly Ile Pro Leu Gly
1               5                   10                  15
Val Asp

<210> SEQ ID NO 61
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 61

Gly Leu Ser Ile Pro Val Gly Tyr Leu Gly Phe Gly Ile Pro Leu Gly
1               5                   10                  15
Leu Pro

<210> SEQ ID NO 62
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 62

Gln Leu Ser Ile Pro Val Gly Tyr Ala Gly Phe Gly Leu Pro Leu Gly
1               5                   10                  15
Ala Pro

<210> SEQ ID NO 63
<211> LENGTH: 18
<212> TYPE: PRT
<213> ORGANISM: Artificial Sequence
<220> FEATURE:
<223> OTHER INFORMATION: Synthetic amino acid - PD1
```

-continued

<400> SEQUENCE: 63

Gln Leu Lys Glu Ile Pro Asp Tyr Val Ser Phe Ala Pro Leu Gly Ala
1               5                   10                  15

Asp Phe

<210> SEQ ID NO 64
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 64

Gly Leu Lys Glu Pro Val Gly Tyr Leu Gly Phe Gly Leu Pro Gly Ala
1               5                   10                  15

Asp Phe

<210> SEQ ID NO 65
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 65

Asn His Ser Glu Ile Pro Asp Phe Leu Gly Tyr Gly Leu Pro Gly Ala
1               5                   10                  15

Asp Phe

<210> SEQ ID NO 66
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 66

Gln Leu Ser Ile Glu Pro Val Phe Leu Gly Tyr Gly Leu Pro Leu Gly
1               5                   10                  15

Leu Asp

<210> SEQ ID NO 67
<211> LENGTH: 18
<212> TYPE: PRT
<213> ORGANISM: Artificial Sequence
<220> FEATURE:
<223> OTHER INFORMATION: Synthetic amino acid - PD1

<400> SEQUENCE: 67

Ala Leu Lys Ile Ser Glu Pro Val Tyr Leu Gly Phe Ala Pro Leu Val
1               5                   10                  15

Gly Asp

<210> SEQ ID NO 68
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 68

Ile Ala Pro Asp Tyr Ser Gln Glu Arg Asp Thr Ile Glu Gly Lys Thr

Pro Val Arg

<210> SEQ ID NO 69
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 69

Ile Ala Pro Asp Tyr Ser Gln Glu Leu Asp Pro Ile Glu Gly Lys Thr
1               5                   10                  15

Pro Val Arg

<210> SEQ ID NO 70
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 70

Ile Ala Pro Asp Tyr Ser Gln Glu Arg Asp Thr Ile Ala Gly Lys Thr
1               5                   10                  15

Pro Val Arg

<210> SEQ ID NO 71
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 71

Ile Ala Pro Asp Tyr Ser Gln Glu Leu Asp Pro Ile Ala Gly Lys Thr
1               5                   10                  15

Pro Val Arg

<210> SEQ ID NO 72
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 72

Ile Ala Pro Asp Tyr Ser Gln Glu Leu Asp Pro Ile Ala Gly Lys Thr
1               5                   10                  15

Pro Val Arg

<210> SEQ ID NO 73
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 73

Ile Ala Ser Asp Tyr Ser Gln Glu Arg Asp Thr Ile Glu Gly Lys Thr
1               5                   10                  15

Pro Val Arg

<210> SEQ ID NO 74
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 74

Ile Leu Pro Asp Tyr Ser Gln Glu Leu Asp Pro Ile Glu Gly Lys Thr
1               5                   10                  15

Pro Val Arg

<210> SEQ ID NO 75
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 75

Val Ala Pro Asp Tyr Ser Gln Glu Arg Asp Thr Ile Ala Gly Lys Thr
1               5                   10                  15

Pro Val Arg

<210> SEQ ID NO 76
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 76

Leu Ala Pro Asp Tyr Lys Gln Glu Leu Asp Pro Ile Ala Phe Lys Thr
1               5                   10                  15

Pro Val Arg

<210> SEQ ID NO 77
<211> LENGTH: 19
<212> TYPE: PRT
<213> ORGANISM: Artificial Sequence
<220> FEATURE:
<223> OTHER INFORMATION: Synthetic amino acid - PD-L1

<400> SEQUENCE: 77

Ile Ala Pro Asp Tyr Ser Gln Glu Leu Asp Pro Ile Val Asn Val Thr
1               5                   10                  15

Pro Val Arg

<210> SEQ ID NO 78
<211> LENGTH: 12
<212> TYPE: PRT
<213> ORGANISM: Artificial Sequence
<220> FEATURE:
<223> OTHER INFORMATION: Synthetic amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

```
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 78

Trp Xaa Glu Xaa Pro Xaa Phe Tyr Xaa Tyr Xaa Ala
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 79

Gln Xaa Ser Asn Xaa Pro Ala Arg Xaa Thr Asp Xaa
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 80

Gln Xaa Ser Asn Xaa Pro Ala Arg Xaa Thr Asp Xaa Gly Pro
1               5                   10

<210> SEQ ID NO 81
<211> LENGTH: 19
<212> TYPE: PRT
<213> ORGANISM: Artificial Sequence
<220> FEATURE:
<223> OTHER INFORMATION: Synthetic amino acid
```

<400> SEQUENCE: 81

Gln Tyr Thr Phe Gly Ser Asn Glu Pro Ala Arg Ser Leu Gly Thr Asp
1               5                   10                  15

Asn Gly Pro

<210> SEQ ID NO 82
<211> LENGTH: 10
<212> TYPE: PRT
<213> ORGANISM: Artificial Sequence
<220> FEATURE:
<223> OTHER INFORMATION: Synthetic amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 82

Trp Xaa Glu Xaa Phe Tyr Xaa Tyr Xaa Ala
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic amino acid

<400> SEQUENCE: 83

Trp Ser Gly Glu Asn Gly Pro Gly Thr Phe Tyr Asp Tyr Glu Ala Cys
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic amino acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature

```
<222> LOCATION: (15)..(15)
<223> OTHER INFORMATION: Xaa can be any naturally occurring amino acid

<400> SEQUENCE: 84

Xaa Tyr Asp Thr Xaa Arg Xaa Pro Asn Ser Xaa Gly Xaa Gln Xaa
1               5                   10                  15
```